United States Patent [19]

Lloyd et al.

[11] Patent Number: 5,934,272

[45] Date of Patent: *Aug. 10, 1999

[54] DEVICE AND METHOD OF CREATING AEROSOLIZED MIST OF RESPIRATORY DRUG

[75] Inventors: Lester J. Lloyd, Orinda; Peter M. Lloyd, Oakland; Reid M. Rubsamen; Jeffrey A. Schuster, both of Berkeley, all of Calif.

[73] Assignee: Aradigm Corporation, Hayward, Calif.

[ * ] Notice: This patent is subject to a terminal disclaimer.

[21] Appl. No.: 08/549,605

[22] Filed: Oct. 27, 1995

Related U.S. Application Data

[63] Continuation-in-part of application No. 08/330,929, Oct. 28, 1994, abandoned, which is a continuation-in-part of application No. 08/011,358, Jan. 29, 1993, abandoned.

[51] Int. Cl.$^6$ .................................................. A61M 11/00
[52] U.S. Cl. ............................... 128/200.22; 128/200.14; 128/204.23
[58] Field of Search .................... 128/200.14, 200.22, 128/203.12, 204.23; 222/95; 239/102.2, 145

[56] References Cited

U.S. PATENT DOCUMENTS

| 3,812,854 | 5/1974 | Michaels et al. | 128/200.16 |
|---|---|---|---|
| 3,923,057 | 12/1975 | Chalon | 128/203.16 |

(List continued on next page.)

FOREIGN PATENT DOCUMENTS

| 0 186 280 | 10/1985 | European Pat. Off. . |
|---|---|---|
| 0 232 235 A2 | 8/1987 | European Pat. Off. . |

(List continued on next page.)

OTHER PUBLICATIONS

Camp, J.P., "Patient–Controlled Analgesia", 1991, AFP Clinical Pharmacology, 44:2145–2150.

Colthorpe, P. et al., "The pharmacokinetics of Pulmonary–Delivered Insulin:A comparison of intratracheal and aerosol administration to the rabbit", 1992, Pharmaceutical Research, 9:764–768.

(List continued on next page.)

*Primary Examiner*—Aaron J. Lewis
*Attorney, Agent, or Firm*—Karl Bozicevic; Bozicevic, Field & Francis LLP

[57] ABSTRACT

Devices, packaging and methodology for efficiently and repeatably creating aerosolized bursts of a formulation of respiratory drug are disclosed. Devices are hand-held, self-contained units which are automatically actuated at the same release point in a patient's inspiratory flow cycle. The release point is automatically determined either mechanically or, more preferably calculated by a microprocessor which receives data from a sensor making it possible to determine inspiratory flow rate and inspiratory volume. The device is loaded with a cassette comprised of an outer housing which holds a package of individual collapsible containers of formulation which comprises a respiratory drug useful in topically treating lung tissue. Actuation of the device forces respiratory drug through a porous membrane of the container which membrane has pores having a diameter in the range of about 0.25 to 6.0 microns. The porous membrane is positioned in alignment with a surface of a channel through which a patient inhales air. The flow profile of air moving through the channel is such that the flow at the surface of the channel is less than the flow rate at the center of the channel. The membrane is designed so that it protrudes outward at all times or is made flexible so that when respiratory drug formulation is forced against and through the membrane the flexible membrane protrudes outward beyond the flow boundary layer of the channel into faster moving air. Because the membrane protrudes into the faster moving air of the channel the particles of aerosol formed are less likely to collide allowing for the formation of a burst of fine aerosol mist with uniform particle size.

8 Claims, 9 Drawing Sheets

OTHER PUBLICATIONS

Daman, H.R., "Pulmonary function testing:Use of the peak expiratory flow rate in an out–patient or office setting", 1984, Journal of Asthma, 21:331–337.

Evans, R. et al., "National trends in the morbidity and mortality of asthma in the US", 1987, Chest, 91(Supp.):65S–74S.

Gourlay, G.K. et al., "Fetanyl blood concentration–analgesic response relationship in the treatment of postoperative pain", 1988, Anesth. Analg. 67:329–337.

Jackson, R. et al., "International trends in asthma mortality: 1970 to 1985", 1988, Chest, 94:914–919.

Jaffe, A.B. et al., Rats self–administer sufentanil in aerosol form.

Janson–Bjerklie, S. et al., "Effect of peak flow information on patterns of self–care in adult asthma", 1988, Heart & Lung, 17:543–549.

Kohler, D., "Aerosols for Systemic Treatment", 1990, Lung, Suppl.:677–684.

Lauber, B.L. et al., "Deposition, Clearance, and Effects in the Lung", Journal of Aerosol Medicine, 4:286.

Lehmann, K.A. et al., "Transdermal fentanyl for the treatment of pain after major urological operations", 1991, Eur. J. Clin. Pharmacol. 41:17–21.

Malo, J. et al., Four–times–a–day dosing frequency is better than a twice–a–day regimen in subjects requiring a high–dose inhaled steroid, budesonide, to control moderate to severe asthma, 1989, Am. Rev. Respir. Dis. 140:624–628.

Mather, J.E., "Pharmacokinetics and patient–controlled analgesia(*)", 1992, Acta Anaesthesiologica Belgica 43:5–20.

Miller, R., "Anaesthesia", (2nd Edition), 1986, Churchill Livingstone, 1:762.

Moses, A.C. et al., Insulin administered intranasally as an insulin–bile salt aerosol–Effectiveness and Reproducibility in Normal and Diabetic Subjects, 1983, Diabetes, 32:1040–1047.

Newman, S.P. et al., "Deposition of pressurized aerosols in the human respiratory tract", 1981, Thorax, 36:52–55.

Newman, S.P. et al., "How should a pressurized β–adrenergic bronchodilator be inhaled?", 1981, Eur. J. Respir. Dis. 62:3–21.

Newman, S.P. et al., "Deposition of pressurized suspension aerosols inhaled through extension devices", 1981, Am. Rev. Respir. Dis. 124:317–320.

Newman, S.P., "Deposition and Effects of Inhalation Aerosols", 1983, (2 ed.), Churchill Livingstone.

Nieminen, M.M., "Aerosol deposition in automatic dosimeter nebulization", 1987, Eur. J. Respir. Dis. 71:145–152.

Nowak, R. et al., Comparison of peak expiratory flow and $FEV_1$ admission criteria for acute bronchial asthma, 1982, Annals of Emergency Medicine, 11:64–69.

Rapp, R.P. et al., Patient–controlled analgesia:A review of effectiveness of therapy and an evaluation of currently available devices, 1989, DICP, The Annals of Pharmacotherapy 23:899–904.

Rosenberg, M., "Patient–controlled analgesia", 1992, J. Oral Maxillofac. Surg. 50:386–389.

Rowbotham, D.J. et al., "A disposable device for patient––controlled analgesia with fentanyl", 1989, Anaesthesia, 44:922–924.

Ryder, E., "The history of patient–controlled analgesia", 1991, Journal of Intravenous Nursing 14:372–381.

Salzman, R.,"Intranasal aerosolized insulin mixed–meal studies and long–term use in type 1 diabetes", 1985, New England Journal of Medicine, 213:1078–1084.

Sears et al., "Increasing asthma mortality—fact or artifact?", 1988, Journal of Allergy and Clinical Immunology, 82:957–960.

Shade, P., "Patient–controlled analgesia:can client education improve outcomes?", 1992, Journal of Advanced Nursing, 17:408–413.

Shim, Chang et al., "Evaluation of the severity of asthma: Patients versus physicians", American Journal of Medicine, 68:11–13.

Smythe, M., "Patient–controlled analgesia:A review", 1992, Pharmacotherapy, 12:132–143.

Spitzer, W.O. et al., "The Use of β–agonists and the risk of death and near death from asthma", 1992, N. Engl. J. Med. 326:501–506.

Wigley, F.M. et al., "Insulin across respiratory mucosae by aerosol delivery", 1971, Diabetes 20:552–556.

Williams, Jr., H., "Expiratory flow rates:Their role in asthma therapy", 1982, Hospital Practice 10:95–110.

Yoshida, H. et al., "Absorption of insulin delivered to rabbit trachea using aerosol dosage form", 1979, J. Pharmaceutical Sciences, 68:670–671.

U.S. PATENT DOCUMENTS

| | | | |
|---|---|---|---|
| 3,991,304 | 11/1976 | Hillsman | 600/538 |
| 4,090,642 | 5/1978 | Baker | 222/94 |
| 4,361,401 | 11/1982 | Smith et al. | 356/36 |
| 4,604,847 | 8/1986 | Moulding, Jr. et al. | 53/75 |
| 4,621,632 | 11/1986 | Bartels et al. | 128/203.27 |
| 4,627,432 | 12/1986 | Newell et al. | 128/203.15 |
| 4,686,231 | 8/1987 | Bender et al. | 514/333 |
| 4,877,989 | 10/1989 | Drews et al. | 310/323 |
| 4,926,852 | 5/1990 | Zoltan et al. | 128/200.23 |
| 4,984,158 | 1/1991 | Hillsman | 128/200.14 |
| 5,167,506 | 12/1992 | Kilis et al. | 434/262 |
| 5,172,686 | 12/1992 | Anthony | 128/203.16 |
| 5,363,842 | 11/1994 | Mishelevich et al. | 128/200.14 |
| 5,394,866 | 3/1995 | Ritson et al. | 128/200.14 |
| 5,404,871 | 4/1995 | Goodman et al. | 128/200.14 |
| 5,450,336 | 9/1995 | Rubsamen et al. | 702/104 |
| 5,497,944 | 3/1996 | Weston et al. | 239/321 |
| 5,743,250 | 4/1998 | Gonda et al. | 128/200.14 |

FOREIGN PATENT DOCUMENTS

| | | |
|---|---|---|
| 0 358 002 A2 | 3/1990 | European Pat. Off. . |
| 0 430 566 A2 | 6/1991 | European Pat. Off. . |
| 2 673 142 | 8/1992 | France . |
| 2 104 393 | 3/1983 | United Kingdom . |
| 2 164 569 | 3/1986 | United Kingdom . |
| 2 255 918 | 11/1992 | United Kingdom . |
| 2 256 805 | 12/1992 | United Kingdom . |
| 90/00015 | 1/1990 | WIPO . |
| WO 90/07333 | 7/1990 | WIPO . |
| WO 91/14468 | 10/1991 | WIPO . |
| 92/07599 | 5/1992 | WIPO . |
| WO 92/09322 | 6/1992 | WIPO . |
| WO 92/15353 | 9/1992 | WIPO . |
| WO 93/17728 | 9/1993 | WIPO . |
| WO 95/01137 | 1/1995 | WIPO . |

DEVICE AND METHOD OF CREATING AEROSOLIZED MIST OF RESPIRATORY DRUG

CROSS REFERENCE TO RELATED APPLICATIONS

This application is a continuation-in-part of our earlier filed application Ser. No. 08/330,929 filed Oct. 28, 1994, now abandoned, which is a continuation-in-part of earlier filed application Ser. No. 08/011,358 filed Jan. 29, 1993, now abandoned, which applications are incorporated herein by reference and to which applications is claimed priority under 35 USC §120.

FIELD OF THE INVENTION

This invention relates generally to devices and methods for creating aerosolized formulations which are useful in treating respiratory disease. More specifically, this invention relates to devices and methods for aerosolizing formulations of respiratory drugs including anti-inflammatory drugs, bronchodilators and enzymes in a controlled and repeatable manner with respect to both particle size and amount.

BACKGROUND OF THE INVENTION

Asthma is a disease effecting approximately 20 million Americans. The death rates from asthma have increased substantially since 1979, increasing for children over five years of age from the period from 1979 to 1982. Hospitalization rates for asthma increased by 50% for adults in that period and by over 200% for the period from 1965 to 1983. Hospitalization rates for black patients are 50% higher for adults and 150% higher for children than the general population. (R. Evans et al., "National Trends in the Morbidity and Mortality of Asthma in the US," *Chest* (1987) 91(6) Sup., 65S–74S). Increasing asthma mortality rates for the same period of time has been documented in other countries. (R. Jackson et al., "International Trends in Asthma Mortality: 1970–1985," *Chest* (1988) 94, 914–19.)

The mainstay for the management of asthma as well as other respiratory diseases in the United States has been inhaled aerosolized medication. The primary aerosolized drugs currently prescribed for respiratory therapy in the United States are anti-inflammatory drugs, bronchodilators and enzymes. These medications can be self-administered by patients using hand held metered dose inhalers (MDIs). Bronchodilators, while useful for the management of an acute asthma attack, are currently not the preferred drugs of choice for long-term asthma management. Aerosolized anti-inflammatory drugs, such as inhaled steroids and cromoglycates, used in conjunction with objective measures of therapeutic outcome are the preferred tools for long-term management of the asthmatic patient. (U.S. Department of Health and Human Services, "Guidelines for the Diagnosis and Management of Asthma," National Asthma Education Program Expert Panel Report, pub. no. 91-3042, August 1991.)

Quantitative spirometry allows clinically relevant indices of pulmonary function to be followed in the asthmatic patient during therapy or for any patient suffering from a respiratory disease. Forced vital capacity, $FEV_1$, peak expiratory flow and mid-expiratory values have all been shown to be useful for following the effect of respiratory therapy. (Quakenboss et al., "The Normal Range of Diurnal Changes in Peak Expiratory Flow Rates: Relationship to Symptoms and Respiratory Disease," *Am Rev Resp Dis* (1991) 143, 323–30; Nowak et al., "Comparison of Peak Expiratory Flow and $FEV_1$: Admission Criteria for Acute Bronchial Asthma," *Annals of Emergency Medicine* (1982) 11, 64–9.) Because spirometry involves recording several parameters with sensitive and complex instrumentation, the peak expiratory flow rate (PEFR) has been adopted as a useful index for inexpensively allowing patients to monitor their own pulmonary function at home. (Darman, "Pulmonary Function Testing; Use of the Peak Expiratory Flow Rate in an Outpatient or Office Setting," *Journal of Asthma* (1984) 21 (5), 331–37.) The use of objective assessment of pulmonary function for managing asthmatic patients is critical because patients and physicians tend to inaccurately assess the patients' own pulmonary conditions. (Shim et al., "Evaluation of Severity of Asthma: Patients versus Physicians," *American Journal of Medicine* (68), 11–13.) The inability of patients and physicians to recognize the signs of a severe asthma attack may be a factor contributing to the observed increasing asthma death rates. (Sears, "Increasing Asthma Mortality—Fact or Artifact?," *Journal of Allergy and Clinical Immunology* (1988) 82, 957–60.) Providing patients with peak expiratory flow measurement information may cause them to manage their own asthma more rationally. (Janson, Bjerkel et al., "Effect of Peak Flow Information on Patterns of Self-Care in Adult Asthma," *Heart Lung* (1988) 17, 543–49; Williams et al., "Expiratory Flow Rates: Their Role in Asthma Therapy," *Hospital Practice* (1982) 10, 95–110.)

A rational program for self-administration of aerosolized asthma therapeutic drugs would include: a) avoidance of overuse of bronchodilators, given that all bronchodilator drugs may be potentially toxic when used in excess (W. Spitter et al., "The Use of B-Agonists and the Risk of Death and Near Death from Asthma," *N Engl J Med* (1992) 326, 501–6); and b) using an anti-inflammatory drug on a prescribed scale which may include regular dosing several times a day (J. L. Malo et al., "Four-times-a-day Dosing Frequency Is Better than Twice-a-day Regimen in Subjects Requiring a High-dose Inhaled Steroid, Budesonide, to Control Moderate to Severe Asthma," *Am Rev Respir Dis* (1989) 140, 624–28).

It is a problem with peak expiratory flow rate monitoring that peak expiratory flow rate data is typically interpreted out of context with aerosolized drug dosing events. For example, a marginally acceptable peak expiratory flow rate data point with that peak expiratory flow rate measurement made one minute following the administration of a bronchodilator has a different meaning than if that same measurement with that same value were made one minute prior to the administration of an aerosolized bronchodilator drug.

It is a problem with peak flow monitoring when used to monitor the long-term therapeutic effect of anti-inflammatory aerosolized asthma therapeutic drugs that peak flow data must be interpreted in the context of aerosolized anti-inflammatory drug dosing events. For example, if the patient's peak expiratory flow rate is deteriorating over a period of weeks when the patient is compliant with his anti-inflammatory aerosolized drug therapy program, this deterioration in objective lung function measurement has a very different meaning than if the patient is failing to take his medication as prescribed.

It is a problem with metered dose inhalers that the patient must record in his diary the time of each drug dosing event. It is a problem with portable peak expiratory flow rate measuring devices that the patient must record each peak flow measurement in a diary. There is a system available allowing metered drug dose inhaler drug dosing events to be automatically recorded. (Nebulizer Chronolog.) There is also an instrument available for printing out the time and value of a peak flow measurement made by a patient at home. It is a problem with these automatic dose logging devices and automatic peak expiratory flow rate logging devices that they do not intercommunicate to allow a definitive analysis of the relationship between drug dosing events and peak flow measurement events. In particular, small differences in the real time clocks contained within the dose logging device and peak flow logging device would make it impossible to determine the temporal relationship of drug dosing events and peak flow monitoring events. When acutely acting bronchodilators are used, a difference of even one or two minutes between the time-based standards used by the drug dosing logging device and the peak flow measurement logging device would introduce unacceptable error in evaluating the relationship of drug dosing and objective pulmonary function measuring events.

It is a problem with these logging devices that when used to monitor a chronic anti-inflammatory aerosolized drug asthma therapy program, the overall compliance of the patient is not easily evaluated. For efficient evaluation of patients in the office setting, an easy-to-read graphical display of long-term compliance with asthma therapy is essential in order to rapidly identify the non-compliant patient and, thus, correctly interpret peak expiratory flow rate data.

SUMMARY OF THE INVENTION

Devices, packaging and methodology for efficiently and repeatably creating aerosolized bursts of a formulation of respiratory drug are disclosed. Devices are hand-held, self-contained units which are automatically actuated at the same release point in a patient's inspiratory flow cycle. The release point is automatically determined either mechanically or, more preferably calculated by a microprocessor which receives data from a sensor making it possible to determine inspiratory flow rate and inspiratory volume. The device is loaded with a cassette comprised of an outer housing which holds a package of individual collapsible containers of formulation comprising a respiratory drug useful in topically treating lung tissue. Actuation of the device forces respiratory drug through a porous membrane of the container which membrane has pores having a diameter in the range of about 0.25 to 6.0 microns. The porous membrane is positioned in alignment with a surface of a channel through which a patient inhales air. The flow rate profile of air moving through the channel is such that the flow rate at the surface of the channel is less than the flow rate at the center of the channel. The membrane is designed so that it protrudes outward at all times or is flexible so that when respiratory drug formulation is forced against and through the membrane the flexible membrane protrudes outward beyond the flow boundary layer of the channel into faster moving air. Because the membrane protrudes into the faster moving air of the channel the particles of aerosol formed are less likely to collide allowing for the formation of a burst of fine aerosol mist with uniform particle size.

Smaller particle sizes are preferred to treat certain areas of the lung. Thus, in one embodiment, after the aerosolized mist is released into the channel energy is actively added to the particles in an amount sufficient to evaporate carrier and thereby reduce particle size. The air drawn into the device is actively heated by moving the air through a heating material which material is pre-heated prior to the beginning of a patient's inhalation. The amount of energy added can be adjusted depending on factors such as the desired particle size, the amount of the carrier to be evaporated, the water vapor content of the surrounding air and the composition of the carrier.

When treating a respiratory disease it is desirable to obtain an aerosolized dose of formulation which will uniformly deposit on all or particular areas of the lung. At times it is desirable to avoid depositing drug in the outer peripheral areas of the lung to limit systemic delivery and emphasize topical treatment of lung tissue. This is obtained per the present invention, in part, by adjusting particle sizes. Particle diameter size is generally about twice the diameter of the pore from which the particle is extruded. In that it is technically difficult to make pores of 2.0 microns or less in diameter the use of evaporation can reduce particle size to 3.0 microns or less even with pore sizes well above 1.5 microns. Energy may be added in an amount sufficient to evaporate all or substantially all carrier and thereby provide particles of dry powdered respiratory drug or highly concentrated respiratory drug formulation to a patient which particles are uniform in size regardless of the surrounding humidity and smaller due to the evaporation of the carrier. Air drawn into the device by the patient may be drawn through a desiccator containing a desiccant which removes moisture from the air thereby improving evaporation efficiency when the carrier is water. Alternatively, water vapor or aerosolized water may be introduced to the channel to saturate inhaled air thereby preventing evaporation of carrier and maintaining particle size. By adding energy some or all carrier can be evaporated. Alternatively, by adding water evaporation can be prevented. Either procedure provides a desired result in that the size of the particles may be modified or maintained regardless of the surrounding humidity of the air where the device is used.

In addition to adjusting particle size, uniform deposition of respiratory drug on lung tissue is obtained by releasing the aerosolized dose at a desired point in the patient's inspiratory flow cycle. To determine such, the patient's inspiratory flow rate is measured and a determination is made of a typical and preferred rate and volume for the release of respiratory drug. To obtain repeatability in dosing the drug is repeatedly released at the same rate and volume as determined in real time. Thus, the method involves measuring for, determining and/or calculating a firing point or drug release decision based on instantaneously (or real time) calculated, measured and/or determined inspiratory flow rate and inspiratory volume points. The amount of drug delivered is maximized based on the amount released when the drug is released at a rate of from about 0.10 to about 2.0 liters/second, and a volume of about 0.15 to about 1.5 liters. Parameters such as rate, volume, and particle size of the aerosolized formulation are adjusted to obtain repeatable dosing of the maximum amount of drug to the desired area of the lung. Lung function is measured and use parameters are adjusted in order to improve lung function.

A primary object of the invention is to provide a method of respiratory treatment using a pocket-sized, hand-held, unitary, integrated drug dispensing device (less than 1 kilogram) designed for the controlled release of respiratory drugs in a repeatable manner.

A feature of the invention is that the drug dispensing device records the precise date, time and amount of drug released at each dosing event.

Another feature of the present invention is that the device is capable of monitoring pulmonary function.

An advantage of the present invention is that the amount and timing of drug released can be cross-referenced with readings on the pulmonary function of the patient in order to provide for means of determining optimal treatment of patients suffering from a respiratory disease.

It is another object of this invention to provide a pocket-sized, single, integrated device for recording the date, time and amount of aerosolized drug delivered at each drug delivery event which device is also capable of monitoring pulmonary function and maintaining a record of the date, time and value of each objective lung function.

It is another object of this invention to provide a device capable of monitoring and recording objective pulmonary function information and displaying such information in a manner integrated with drug dosing event information so as to provide a means of evaluating quantitative, objective measures of pulmonary function in the context of actual administered therapy.

It is another object of this invention to show that the evaluation of pulmonary function in light of actual patient compliance only has meaning if drug dosing events are actually associated with patient inspiration and firing of the aerosolized drug into the patient's mouth.

It is another object of this invention to show that interpretation of pulmonary function data in the context of actual drug dosing events allows physicians to counsel patients accurately with regard to avoidance of overdosing of potentially toxic inhaled aerosolized drugs such as bronchodilators and gives physicians a tool for quantitatively advising patients regarding adjustments to their long-term anti-inflammatory aerosolized drug treatment program and/or long term enzyme treatment program.

It is an object of this invention to describe a method of aerosolized delivery of respiratory drug in a safe and effective manner.

An advantage of the present invention is that it can be used for ambulatory patients with respiratory disease.

Another object is to provide a method of respiratory therapy for ambulatory patients wherein an aerosolized formulation of a respiratory drug is repeatedly delivered to the patient at the same measured inspiratory volume (in the range of 0.15 to 1.5 liters) and the same measured inspiratory flow rate (in the range of 0.1 to 2.0 liters per sec).

An object of the invention is to provide a container which holds an aerosolizable formulation of respiratory drug which container comprises a porous membrane which protrudes outward in a stationary state or on the application of force forming a convex surface when drug formulation is forced against and through the membrane.

Another object is to provide a method for creating an aerosol of respiratory drug formulation which comprises drawing air over a surface of a porous membrane in a channel and forcing formulation against the membrane so as to protrude the membrane through a flow boundary layer into faster moving air of the channel.

Another object of the invention is to adjust particle size by adding energy to the particles in an amount sufficient to evaporate carrier and reduce total particle size.

Another object is to provide a drug delivery device which includes a desiccator for drying air in a manner so as to remove water vapor and thereby provide consistent particle sizes even when the surrounding humidity varies.

Another object is to provide a device for the delivery of aerosols which measures humidity via a solid state hygrometer.

A feature of the invention is that drug can be dispersed or dissolved in a liquid carrier such as water and dispersed to a patient as dry or substantially dry particles.

Another advantage is that the size of the particles delivered will be independent of the surrounding humidity.

These and other objects, advantages and features of the present invention will become apparent to those skilled in the art upon reading this disclosure in combination with drawings wherein like numerals refer to like components throughout.

DETAILED DESCRIPTION OF THE PREFERRED EMBODIMENTS

Figure 1:
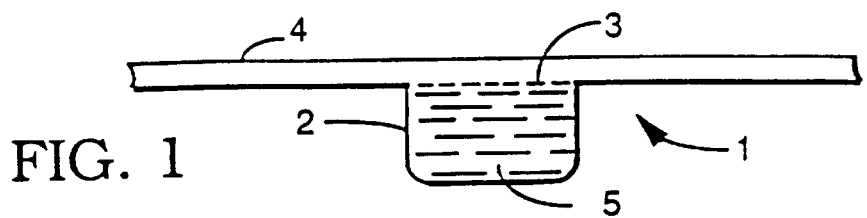
FIG. 1 is a cross-sectional view of a container of the invention.

Before the present method of treating patients suffering from a respiratory disease and devices, containers and formulations used in connection with such are described, it is to be understood that this invention is not limited to the particular methodology, devices, containers and formulations described, as such methods, devices, containers and formulations may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural referents unless the context clearly dictates otherwise. Thus, for example, reference to "a formulation" includes mixtures of different formulations, reference to "an asthma attack" includes one or more of such events, and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference to describe and disclose specific information for which the reference was cited in connection with.

Definitions

The term "respiratory drug" shall be interpreted to mean any pharmaceutically effective compound used in the treatment of any respiratory disease and in particular the treatment of diseases such as asthma, bronchitis, emphysema and cystic fibrosis. Useful "respiratory drugs" include those which are listed within the Physician's Desk Reference (most recent edition). Such drugs include beta adrenergic agonists which include bronchodilators including albuterol, isoproterenol sulfate, metaproterenol sulfate, terbutaline sulfate, pirbuterol acetate, salmeterol xinotoate, formotorol; steroids including beclomethasone dipropionate, flunisolide, fluticasone, budesonide and triamcinolone acetonide and also includes peptide non-adrenergic non-cholinergic neurotransmitters and anticholinergics. Anti-inflammatory drugs used in connection with the treatment of respiratory diseases include steroids such as beclomethasone dipropionate, triamcinolone acetonide, flunisolide and fluticasone. Other anti-inflammatory drugs include cromoglycates such as cromolyn sodium. Other respiratory drugs which would qualify as bronchodilators include anticholenergics including ipratropium bromide. Other useful respiratory drugs include leukotrine (LT) inhibitors, vasoactive intestinal peptide (VIP), tachykinin antagonists, bradykinin antagonists, endothelin antagonists, heparin furosemide, anti-adhesion molecules, cytokine modulators, biologically active endonucleases, recombinant human (rh) DNase compounds, α antitrypsin and disodium cromoglycate (DSCG). The present invention is intended to encompass the free acids, free bases, salts, amines and various hydrate forms including semi-hydrate forms of such respiratory drugs and is particularly directed towards pharmaceutically acceptable formulations of such drugs which are formulated in combination with pharmaceutically acceptable excipient materials generally known to those skilled in the art—preferably without other additives such as preservatives. Preferred drug formulations do not include additional components such as preservatives which have a significant effect on the overall formulation. Thus preferred formulations consist essentially of pharmaceutically active drug and a pharmaceutically acceptable carrier (e.g., water and/or ethanol). However, if a drug is liquid without an excipient the formulation may consist essentially of the drug which has a sufficiently low viscosity that it can be aerosolized using a dispenser of the present invention.

The term "dosing event" shall be interpreted to mean the administration of respiratory drug to a patient in need thereof by the intrapulmonary route of administration (i.e., inhaling aerosolized particles into the lung) which event may encompass one or more releases of respiratory drug formulation from an respiratory drug dispensing device over a period of time of 15 minutes or less, preferably 10 minutes or less, and more preferably 5 minutes or less, during which period multiple inhalations may be made by the patient and multiple doses of respiratory drug may be released and inhaled. A dosing event shall involve the administration of respiratory drug formulation to the patient in an amount of about 10 $\mu$l to about 1,000 $\mu$l in a single dosing event which may involve the release of from about 100 $\mu$l to about 10,000 $\mu$l of respiratory drug formulation from the device. In that the drug is dissolved in a carrier to form the formulation the amount of drug delivered may be very small and will vary with the concentration of drug in the carrier.

The term "velocity of the drug" or "velocity of particles" shall mean the average speed of particles of respiratory drug formulation moving from a release point such as a porous membrane or a valve to a patient's mouth. In a preferred embodiment the velocity of the particles is zero or substantially zero in the absence of flow created by patient inhalation.

The term "bulk flow rate" shall mean the average velocity at which air moves through a channel considering that the flow rate is at a maximum in the center of the channel and at a minimum at the inner surface of the channel.

The term "flow boundary layer" shall mean a set of points defining a layer above the inner surface of a channel through which air flows wherein the air flow rate below the boundary layer is substantially below the bulk flow rate, e.g., 50% or less than the bulk flow rate.

The term "carrier" shall mean a liquid, flowable, pharmaceutically acceptable excipient material which a respiratory drug is suspended in or more preferably dissolved in. Useful carriers do not adversely interact with the respiratory drug and have properties which allow for the formation of aerosolized particles preferably particles having a diameter in the range of 0.5 to 12.0 microns when a formulation comprising the carrier and respiratory drug is forced through pores having a diameter of 0.25 to 6.0 microns. Preferred carriers include water, ethanol and mixtures thereof. Other carriers can be used provided that they can be formulated to create a suitable aerosol and do not adversely effect the respiratory drug or human lung tissue.

The term "measuring" describes an event whereby either the inspiratory flow rate or inspiratory volume of the patient is measured in order to determine an optimal point in the inspiratory cycle at which to release aerosolized drug. An actual measurement of both rate and volume may be made or the rate can be directly measured and the volume calculated based on the measured rate. It is also preferable to continue measuring inspiratory flow during and after any drug delivery and to record inspiratory flow rate and volume before, during and after the release of drug. Such reading makes it possible to determine if drug was properly delivered to the patient.

The term "monitoring" event shall mean measuring lung functions such as inspiratory flow, inspiratory flow rate, and/or inspiratory volume so that a patient's lung function as defined herein, can be evaluated before and/or after drug delivery thereby making it possible to evaluate the effect of respiratory drug delivery on the patient's lung function.

The term "inspiratory flow rate" shall mean a value of air flow rate determined, calculated or measured based on the speed of the air passing a given point in a measuring device assuming atmospheric pressure ±5% and a temperature in the range of about 10° C. to 40° C.

The term "inspiratory flow" shall be interpreted to mean a value of air flow calculated based on the speed of the air passing a given point along with the volume of the air that has passed that point with the volume calculation being based on integration of the flow rate data and assuming atmospheric pressure, ±5% and temperature in the range of about 10° C. to about 40° C.

The term "inspiratory volume" shall mean a determined, measured or calculated volume of air passing a given point into the lungs of a patient assuming atmospheric pressure ±5% and a temperature in the range of 10° C. to 40° C.

The term "inspiratory flow profile" shall be interpreted to mean data calculated in one or more events measuring inspiratory flow and cumulative volume, which profile can be used to determine a point within a patient's inspiratory cycle which is optimal for the release of drug to be delivered to a patient. An optimal point within the inspiratory cycle for the release of drug is based, in part, on a point within the inspiratory cycle likely to result in the maximum delivery of drug and based, in part, on a point in the cycle most likely to result in the delivery of a reproducible amount of drug to the patient at each release of drug. Repeatability of the amount delivered is the primary criterion and maximizing the amount delivered is an important but secondary criterion. Thus, a large number of different drug release points might be selected and provide for repeatability in dosing provided the selected point is again selected for subsequent releases. To insure maximum drug delivery the point is selected within given parameters.

The term "therapeutic index" refers to the therapeutic index of a drug defined as $LD_{50}/ED_{50}$. The $LD_{50}$ (lethal dose, 50%) is defined as the dose of a drug which kills 50% of the tested animals, and the $ED_{50}$ is defined as the effective dose of the drug for 50% of the individuals treated. Drugs with a therapeutic index near unity (i.e. $LD_{50}/ED_{50}$ is approximately equal to 1) achieve their therapeutic effect at doses very close to the toxic level and as such have a narrow therapeutic window, i.e. a narrow dose range over which they may be administered.

The terms "formulation" and "liquid formulation" and the like are used interchangeably herein to describe any pharmaceutically active respiratory drug with a pharmaceutically acceptable carrier in flowable liquid form having properties such that it can be aerosolized to particles having a diameter of 0.5 to 12.0 microns. Such formulations are preferably solutions, e.g. aqueous solutions, ethanoic solutions, aqueous/ethanoic solutions, saline solutions, colloidal suspensions and microcrystalline suspensions. Formulations can be solutions or suspensions of drug in a low boiling point propellant. Preferred formulations are drug(s) dissolved in water.

The terms "lung function" and "pulmonary function" are used interchangeably and shall be interpreted to mean physically measurable operations of a lung including but not limited to (1) inspiratory and (2) expiratory flow rates as well as (3) lung volume. Methods of quantitatively determining pulmonary function are used to measure lung function. Quantitative determination of pulmonary function may be important when delivering respiratory drugs in order to determine effectiveness. Methods of measuring pulmonary function most commonly employed in clinical practice involve timed measurement of inspiratory and expiratory maneuvers to measure specific parameters. For example, forced vital capacity (FVC) measures the total volume in liters exhaled by a patient forcefully from a deep initial inspiration. This parameter, when evaluated in conjunction with the forced expired volume in one second ($FEV_1$), allows bronchoconstriction to be quantitatively evaluated. A problem with forced vital capacity determination is that the forced vital capacity maneuver (i.e. forced exhalation from maximum inspiration to maximum expiration) is largely technique dependent. In other words, a given patient may produce different FVC values during a sequence of consecutive FVC maneuvers. The FEF 25-75 or forced expiratory flow determined over the mid-portion of a forced exhalation maneuver tends to be less technique dependent than the FVC. Similarly, the $FEV_1$ tends to be less technique dependent than FVC. In addition to measuring volumes of exhaled air as indices of pulmonary function, the flow in liters per minute measured over differing portions of the expiratory cycle can be useful in determining the status of a patient's pulmonary function. In particular, the peak expiratory flow, taken as the highest air flow rate in liters per minute during a forced maximal exhalation, is well correlated with overall pulmonary function in a patient with asthma and other respiratory diseases. The present invention carries out treatment by administering drug in a drug delivery event and monitoring lung function in a monitoring event. A series of such events may be carried out and repeated over time to determine if lung function is improved.

Each of the parameters discussed above is measured during quantitative spirometry. A patient's individual performance can be compared against his personal best data, individual indices can be compared with each other for an individual patient (e.g. $FEV_1$ divided by FVC, producing a dimensionless index useful in assessing the severity of acute asthma symptoms), or each of these indices can be compared against an expected value. Expected values for indices derived from quantitative spirometry are calculated as a function of the patient's sex, height, weight and age. For instance, standards exist for the calculation of expected indices and these are frequently reported along with the actual parameters derived for an individual patient during a monitoring event such as a quantitative spirometry test.

The term "substantially dry" shall mean that particles of formulation include an amount of carrier (e.g. water or ethanol) which is equal to (in weight) or less than the amount of drug in the particle.

The term "respiratory disease" shall be interpreted to mean any pulmonary disease or impairment of lung function. Such diseases include restrictive and obstructive disease and diseases such as emphysema which involve abnormal distension of the lung frequently accompanied by impairment of heart action. Restrictive diseases tend to limit the total volume of air that a patient is able to exchange through inspiration and expiration. Restrictive disease, such as can be present in certain types of fibrotic processes, can therefore be detected by reduced FVC indices. Obstructive disease, such as is present in patients with asthma, tends not to affect the total volume of air exchangeable through inspiration and expiration but rather the amount of time required for forced exhalation of air. In particular, the $FEV_1$ is markedly reduced in patients with acute asthma symptoms. More specifically, the $FEV_1$, when taken as a ratio of FVC (i.e. $FEV_1$ divided by FVC), is markedly reduced in patients with acute asthma. In addition to increasing the amount of time required for a full forced expiration, the presence of acute bronchoconstrictive disease tends to decrease the peak expiratory flow measured over a typical forced exhalation. The respiratory disease is understood to be "treated" if lung function is improved even if the improvement is temporary.

The terms "aerosolized particles" and "aerosolized particles of formulation" shall mean particles of formulation comprised of pharmaceutically active respiratory drug and carrier which are formed upon forcing the formulation through a nozzle which nozzle is preferably in the form of a flexible porous membrane. The particles have a size which is sufficiently small such that when the particles are formed they remain suspended in the air for a sufficient amount of time such that the patient can inhale the particles into the patient's lungs. Preferably, the particles have a size in the range of 0.5 micron to about 12 microns having been created by being forced through the pores of a flexible porous membrane which pores have a diameter in the range of about 0.25 micron to about 6.0 microns—the pores being present on the membrane in an amount of about ten to 10,000 pores over an area in size of from about 1 sq. millimeter to about 1 sq. centimeter.

General Methodology

The invention is the intrapulmonary delivery of respiratory drug to the patient in a controlled and repeatable manner. The device of the invention provides a number of features which make it possible to achieve the controlled and repeatable dosing procedure required for the treatment of respiratory diseases such as asthma. Specifically, one should adjust:

(1) the release point within a patient's inspiratory flow rate inside a range of about 0.10 to about 2.0 liters/second preferably about 0.2 to about 1.8 liters per sec. and more preferably 0.15 to 1.7 liters per sec;

(2) the release point within a patient's inspiratory volume of about 0.15 to about 2.0 liters preferably 0.15 to 0.8 liters and more preferably 0.15 to about 0.4 liters;

(3) particle size for systemic delivery in a range of about 0.5 to 6 microns and more preferably 0.5 to about 3 microns; and for pulmonary delivery 0.5 to 12 microns, preferably 2.0 to 7.0 microns, more preferably 2.0 to 5.0 microns;

(4) the concentration of the drug in the carrier in the range of from about 0.01% to about 12.5%;

(5) the amount of heat added to the air to be about 20 Joules to about 100 Joules and preferably 20 Joules to about 50 Joules per 10 $\mu$l of formulation;

(6) the relative volume of air added by patient inhalation per 10 $\mu$l of formulation at about 100 ml to 2 l and preferably about 200 ml to 1 liter for evaporation; and without evaporation 50–750 ml, preferably 200–400 ml;

(7) the rate of vibration of the porous membrane from 575 to 17,000 kilohertz;

(8) pore size to a range of about 0.25 to about 6.0 microns in diameter preferably 0.5 to 3 microns and more preferably 1–2 microns;

(9) viscosity of the formulation to a range of from about 25% to 1,000% of the viscosity of water;

(10) extrusion pressure to a range of about 50 to 600 psi and preferably 100 to 500 psi;

(11) ambient temperature to 15° C. to 30° C. and ambient pressure between 1 atmosphere and 75% of 1 atmosphere;

(12) the ratio of liquid carriers to each other to be consistent;

(13) the solubility of drug to carrier to use highly soluble drugs;

(14) the desiccator to maximize removal of water vapor from air;

(15) the shape of the pore opening to be circular in diameter and conical in cross-section with the ratio of the diameter of the small to large end of the cone being about ½ to 1/20, and the shape of the porous membrane to an elongated oval;

(16) the thickness of the membrane to 5 to 200 microns; preferably 10–50 microns;

(17) the membrane to have a convex shape or to be flexible so that it protrudes outward in a convex shape beyond the flow boundary layer when formulation is forced through it; and

(18) the firing point to be at substantially the same point at each release for the parameters (1–17), i.e., each release of drug is at substantially the same point so as to obtain repeatability of dosing.

Respiratory drug is automatically aerosolized upon receipt of a signal from a microprocessor programmed to send a signal when data is received from a monitoring device such as an airflow rate monitoring device. A patient using the device withdraws air from a mouthpiece and the inspiratory flow rate as well as the inspiratory volume of the patient are determined one or more times in a monitoring event which determines a preferred point in an inhalation cycle for the release of a dose of respiratory drug. Inspiratory flow rate and volume are each determined and recorded in one or more monitoring events for a given patient in order to develop an inspiratory flow profile for the patient. The recorded information is analyzed by the microprocessor in order to deduce a preferred point within the patient's inspiratory cycle for the release of respiratory drug with the preferred point being calculated based on the most likely point to result in a reproducible delivery event.

It is pointed out that the device of the present invention can be used to, and actually does, improve the efficiency of drug delivery. However, this is a secondary feature. The primary feature is the reproducibility of the release of a tightly controlled amount of drug at a particular point in the respiratory cycle so as to assure the delivery of a controlled and repeatable amount of drug to the lungs of each individual patient. Other secondary features include the ability to obtain a wide dispersion pattern of the drug in the lungs or direct the drug to particular areas of the lung.

The combination of automatic control of the release of aerosols, combined with frequent monitoring events in order to calculate the optimal flow rate and time for the release of a respiratory drug, combine to provide a repeatable means of delivering respiratory drug to a patient. In that aerosol is released automatically and not manually, it can be predictably and repeatedly released to provide a preprogrammed measured amount of aerosol at that particular dosing event. Because dosing events are preferably preceded by monitoring events, the amount of respiratory drug released and/or the point in the inspiratory cycle of the release can be readjusted based on the particular condition of the patient. For example, if the patient is suffering from a condition which allows for a certain degree of pulmonary insufficiency, such will be taken into account in the monitoring event by the microprocessor which will readjust the amount and/or point of release of the respiratory drug in a manner calculated to provide for the administration of the same amount of respiratory drug to the patient at each dosing event.

Drug Delivery with Disposable Container

FIG. 1 is a cross-sectional view of a container 1 of the invention which is shaped by a collapsible wall 2. The container 1 has an opening covered by a flexible porous membrane 3 which is covered by a removable layer 4. The membrane 3 may be rigid and protrude upward in a convex configuration away from the formulation 5. When the layer 4 is removed the wall 2 can be collapsed thereby forcing the respiratory drug formulation 5 against the flexible porous membrane 3 which will then protrude outward in a convex shape.

Figure 2:
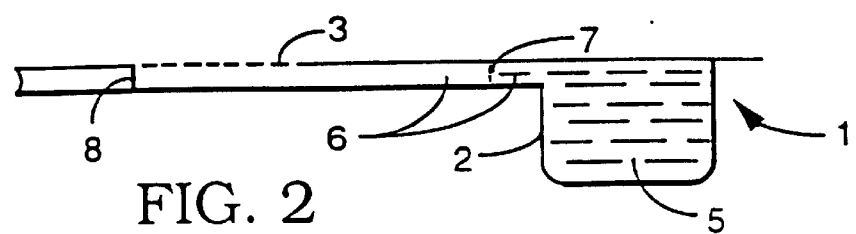
FIG. 2 is a cross-sectional view of a preferred embodiment of a container of the invention.

FIG. 2 is a cross-sectional view of a more preferred embodiment of a container 1 of the invention. The container is shaped by a collapsible wall 2. The container 1 includes an opening which leads to an open channel 6 which channel 6 includes an abutment 7 which is broken upon the application of force created by formulation 5 being forced from the container. When the abutment 7 is broken the formulation 5 flows to an area adjacent to the flexible porous membrane 3 and is prevented from flowing further in the channel 6 by a non-breakable abutment 8.

Figure 3:
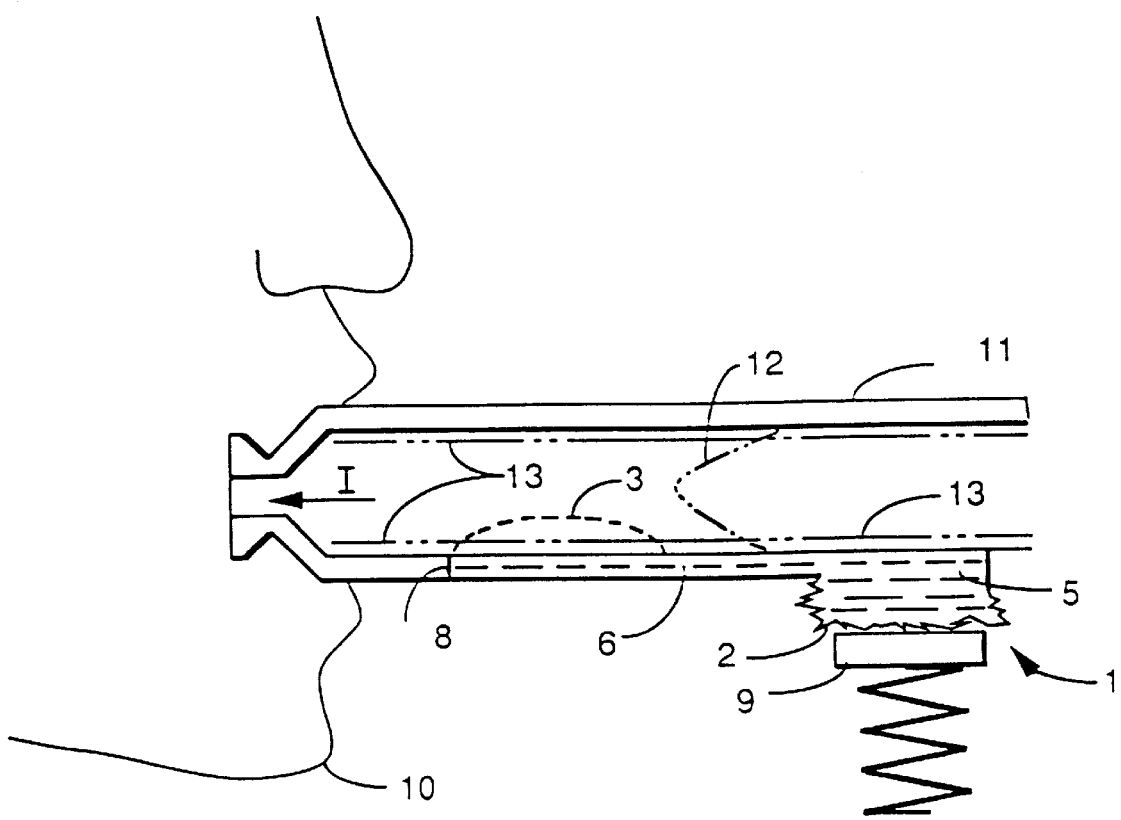
FIG. 3 is a cross-sectional view of the container of FIG. 2 in use in a channel of a drug delivery device.

FIG. 3 is a cross-sectional view of the container 1 of FIG. 2 in use. The wall 2 is being crushed by a mechanical component such as the piston 9 shown in FIG. 3. The piston may be driven by a spring, compressed gas, or a motor connected to gears which translate the electric motor's circle motion to linear motion. The formulation is forced into the open channel 6 (breaking the abutment 7 shown in FIG. 2) and against and through the membrane 3 causing the membrane 3 to protrude outward into a convex configuration as shown in FIG. 3.

The piston 9 has been forced against the container wall 2 after a patient 10 begins inhalation in the direction of the arrow "I". The patient 10 inhales through the mouth from a tubular channel 11. The velocity of the air moving through the flow path 29 of the channel 11 can be measured across the diameter of the channel to determine a flow profile 12, i.e., the air flowing through the channel 11 has a higher velocity further away from the inner surface of the channel. The air velocity immediately adjacent to the inner surface of the channel 11 (i.e., infinitely close to the surface) is very slow (i.e., approaches zero). A flow boundary layer 13 defines a set of points below which (in a direction from the channel center toward the inner surface of the channel) the flow of air is substantially below the bulk flow rate i.e., 50% or less than the bulk flow rate.

To allow air to flow freely through the channel 11 the upper surface of the flexible porous membrane 3 is substantially flush with (i.e., in substantially the same plane as) the inner surface of the channel 11. Thus, if the membrane 3 remained in place when the formulation 5 move through the pores the formulation would be released into the slow moving or substantially "dead air" below the boundary layer 13. However, the membrane 3 protrudes outward through the boundary layer 13 into the faster moving air. This is desirable in that it aids in avoiding the agglomulation of particles. More specifically, when formulation exits the pores the formulation naturally forms spherical particles. Those particles slow down due to the frictional resistance created by the air through which the particles must travel. The particles existing behind them can face reduced air friction because the preceding particle have moved the air aside. Thus later released particles catch up with and merge into the earlier released particles. This can cause a chain reaction resulting in the formation of large particles which can not be readily inhaled into the lung—e.g., the formation of particles having a diameter of more than about 12.0 microns.

A plan view of a simple embodiment of a drug delivery device 40 of the present invention is shown within FIG. 4. The device 40 is loaded and operates with a plurality of interconnected disposable containers 1 which form a package 46. Before describing the details of the individual components of the device 40, a general description of the device and its operation is in order.

Conventional metered dose inhalers and nebulizers suffer from a number of disadvantages. These disadvantages result in the inability to use these devices to repeatedly deliver the same amount of drug to a patient. The disadvantages are due, in part, to the inability to control particle size—especially when the device is used in diverse environments with greatly different humidity conditions or when differing amounts of drug are delivered into a fixed amount of air or similar quantities of drug are delivered into differing amounts of air. By adding sufficient energy to the particles to evaporate any carrier particle size is reduced to a uniform minimum and any humidity variations do not affect particle variability. Further the drug dispensing device of the present invention preferably includes electronic and/or mechanical components which eliminate direct user actuation of drug release. More specifically, the device preferably includes a means for measuring inspiratory flow rate and inspiratory volume and sending an electrical signal as a result of the simultaneous measurement of both (so that drug can be released at the same point each time) and also preferably includes a microprocessor which is programmed to receive, process, analyze and store the electrical signal of the means for measuring flow and upon receipt of signal values within appropriate limits sending an actuation signal to the mechanical means which causes drug to be extruded from the pores of the porous membrane.

The device 40 shown in FIG. 4 is loaded with a disposable package 46. To use the device 40 a patient (see FIG. 3) inhales air from the mouthpiece 30. The air drawn in through the opening 38 (and optionally the desiccator 41) flows through the flow path 29 of the channel 11. The disposable package 46 is comprised of a plurality of disposable containers 1. Each container 1 includes a drug formulation 5 and is covered by the porous membrane 3. An air-heating mechanism 14 located in the flow path 29. The air heating mechanism 14 is preferably positioned such that all or only a portion of the air flowing through the path 29 will pass by the heater, e.g., flow vent flaps can direct any desired portion of air through the heater 14. The heat is preferably turned on for 30 sec or less prior to inhalation and turned off after drug delivery to conserve power.

The device 40 is a hand-held, portable device which is comprised of (a) a device for holding a disposable package with at least one but preferably a number of drug containers, and (b) a mechanical mechanism for forcing the contents of a container (on the package) through a porous membrane. The device preferably further includes (c) a heating mechanism for adding energy to the air flow into which particles are released, (d) a monitor for analyzing the inspiratory flow of a patient, (e) a switch for automatically releasing or firing the mechanical means after the inspiratory flow rate and/or volume reaches a predetermined point (f) a means for measuring ambient temperature and humidity and (g) a source of power e.g., conventional batteries.

The device for holding the disposable package may be nothing more than a narrow opening created between two outwardly extending bars 42 and 82 or may include additional components such as one or more wheels, sprockets or rollers notably mounted on the end(s) of such bars. The rollers may be spring mounted so as to provide constant pressure against the surface(s) of the package. The device may also include a transport mechanism which may include providing drive power to the roller(s) so that when they are rotated, they move the package from one container to the next. The power source 43 driving the roller(s) is programmed via the microprocessor 26 to rotate the rollers only enough to move the package 39 from one container 1 to the next. In order to use the device 40, the device 40 must be "loaded," i.e. connected to a package 39 which includes drug dosage units having liquid, flowable formulations of pharmaceutically active drug therein. The entire device 40 is self-contained, light weight (less than 1 kg preferably less than 0.5 kg loaded) and portable. The power source 43 is preferably in the form of standard alkaline batteries. Two 9 volt batteries could supply the heat required to heat the air which contacts the particles by about 20° C. for about 100 doses (see FIGS. 5 and 6 re energy required).

The formulation is preferably heated after the formulation has been forced through the pores of the membrane 3 and aerosolized i.e., energy is preferably added by heating the surrounding air by means of the air-heating mechanism 14 positioned anywhere within the flow path 29 with the heater positioned after the porous membrane. The amount of energy added by the formulation heating mechanism 45 or air-heating mechanism 5 is controlled by the microprocessor 26 based on the amount of formulation in the container 1 and other factors such as the concentration of the drug and surrounding humidity. A hygrometer 50 and thermometer 51 are electrically connected to the microprocessor 26 allowing the amount of heat to be added to be adjusted based on ambient humidity and temperature.

Potent drugs which are highly soluble in water, ethanol and/or mixtures thereof are particularly useful with the present invention in that such drugs can be used in small amounts in high concentration and thus require less energy to obtain evaporation of the carrier. Particles having a diameter of 6.3 microns can be formed and subjected to evaporation to obtain a particle of one micron in diameter. In the respiratory track this one micron particle would be expected to grow to a 3 micron particle due to moisture added from the high humidity environment of the respiratory tract.

Figure 5:
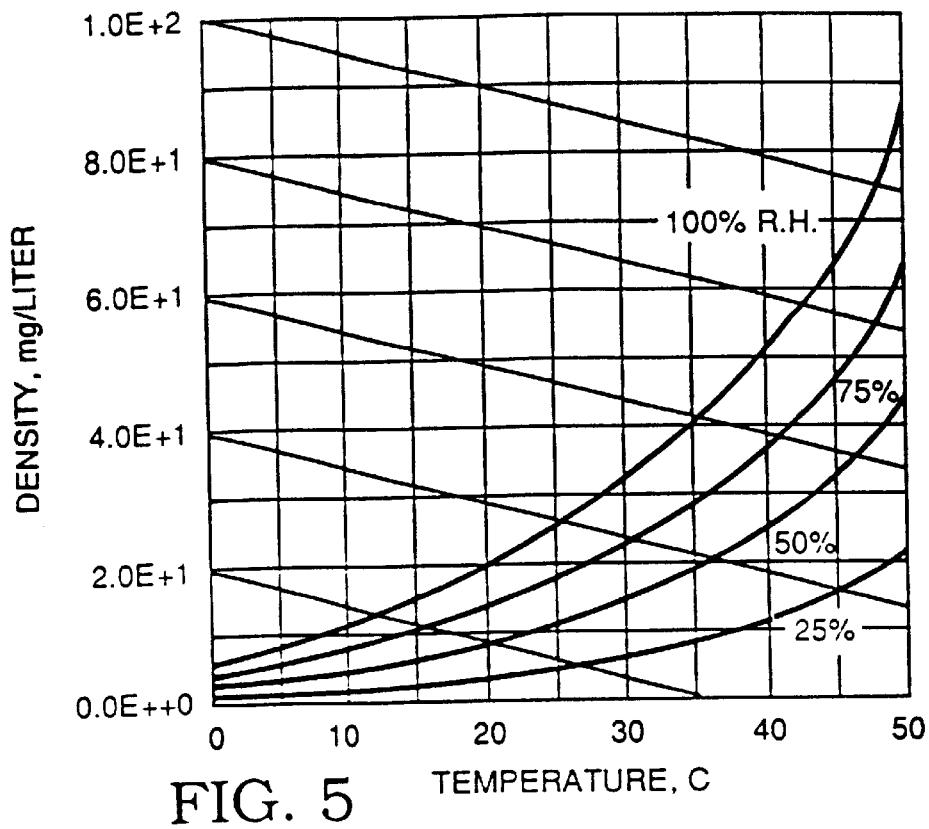
FIG. 5 is a graph plotting the density of water vapor in air versus temperature.

FIG. 5 is a graph which can be used in calculating the amount of energy needed to control the size of delivered droplets by controlling the amount of evaporation of carrier from the aerosolized droplets. The graph of FIG. 5 contains two types of information, the density of evaporated water vs. temperature and relative humidity, and the cooling of the air as the water evaporates. The four lines that show a rapid increase with temperature portray the density of water vapor in air, at 25, 50, 75, and 100% relative humidity. The 100% relative humidity curve represents the maximum number of milligrams of water that can be evaporated per liter of air. The diagonal lines show the temperature change of the air as the water droplets evaporate (hereafter called the air mass trajectory curves). As the evaporation proceeds, the density and temperature will change by moving parallel to these curves. To calculate these curves, air density of 1.185 grams/liter, air specific heat of 0.2401 calories/gram, and water latent heat of vaporization of 0.583 cal/mg were assumed. These values imply that a liter of air will cool 2 celsius degrees for every milligram of water evaporated, i.e. evaporating 10 micro-liters will cool a liter of air 20 celsius degrees.

FIG. 5 can be used to calculate the amount of preheating needed to evaporate all or substantially all of the carrier in the aerosolized particles. As an example, assume the initial ambient conditions are 25° C. and 50% relative humidity. Further, assume that one wants to evaporate 10 μl (10 mgs) of water from an aqueous drug solution. Finally, assume the final relative humidity is 75%. Under these conditions the aqueous carrier would not evaporate completely. More specifically, the final particles would contain approximately equal amounts of drug and water. To calculate the amount of energy to add for this delivery manoeuver, refer to FIG. 5. Locate the point corresponding to 25° C. and 50% relative humidity. Move up by 10 milligrams, the amount of water to be evaporated. Now move to the left until the 75% RH curve is crossed. This occurs at about 29° C. These conditions (75% RH and 29° C.) represent the condition of the air as delivered to the patient. However, still more energy must be added to make up for the cooling of the air as the water evaporates. To calculate this amount of heat, move parallel to the air mass trajectory curves (downward and to the right) until the initial ambient water vapor density is reached, at approximately 47° C. Thus, sufficient heat to warm the air by 22° C. must be added to achieve near complete evaporation.

Figure 6:
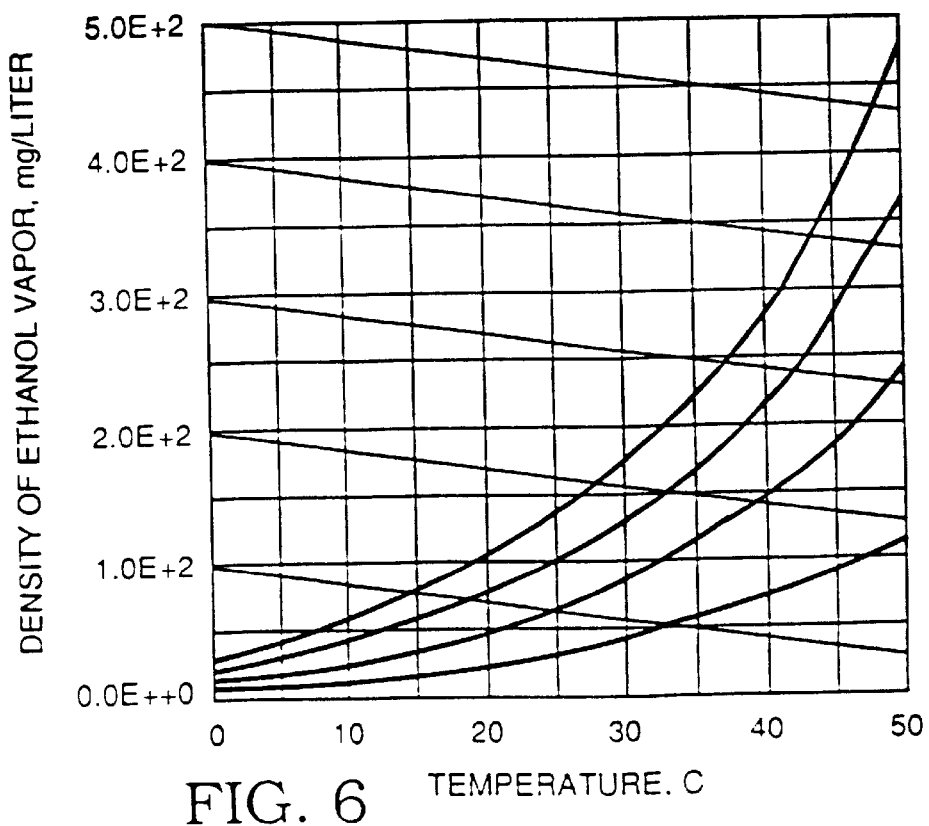
FIG. 6 is a graph plotting the density of ethanol vapor in air versus temperature.

FIG. 6 includes similar information with respect to ethanol which can be used in a similar manner. FIG. 5 shows the density of water vapor in air at 25, 50 and 75° C. and 100% saturation with the air mass trajectory during evaporation also shown. The same is shown in FIG. 6 for the density of ethanol in air.

The evaporation and growth rates of aqueous droplets is a function of their initial diameter, the amount of drug dissolved therein (concentration) and the ambient relative humidity. The determining factor is whether the water vapor concentration at the surface of the droplet is higher or lower than that of the surrounding air. Because the relative humidity at the surface of a particle (i.e. droplet of aerosolized formulation) is close to 100% for all the high concentration formulations, a five micron droplet will evaporate to a 1 micron dry particle in 0% humidity in less than 20 ms. However, if a particle of drug 1 micron diameter is inhaled into the lungs (99.5% humidity) it will grow to about 3 microns in diameter in approximately one second by accumulating water from the humid lung environment.

The opening 38 may have a desiccator 41 positioned therein which desiccator includes a material which removes water vapor from air being drawn into the flow path 29. By reducing or more preferably eliminating water vapor from the air any water in particles of formulation can be more efficiently evaporated. Further, the particles delivered to the patient will have a smaller and more uniform size even if energy is not added to cause evaporation of water from the particles of the formulation.

The device may include a mouth piece 30 at the end of the flow path 29. The patient inhales from the mouth piece 30 which causes an inspiratory flow to be measured by flow sensor 31 within the flow path which path may be, and preferably is, in a non-linear flow-pressure relationship. This inspiratory flow causes an air flow transducer 37 to generate a signal. This signal is conveyed to a microprocessor which is able to convert, continuously, the signal from the transducer 37 in the inspiratory flow path 29 to a flow rate in liters per minute. The microprocessor 26 can further integrate this continuous air flow rate signal into a representation of cumulative inspiratory volume. At an appropriate point in the inspiratory cycle, the microprocessor can send a signal to send power from the power source 43 to the air-heating mechanism 14 which uses information from the hygrometer 50, thermometer 51 and particle size and amount of formulation. The microprocessor also sends a signal to an actuator which causes the mechanical means (e.g., the piston 24) to force drug from a container of the package into the inspiratory flow path 29 of the device and ultimately into the patient's lungs. After being released, the drug and carrier will pass through a porous membrane 3 to aerosolize the formulation and thereafter enter the lungs of the patient.

Preferred Flow Rates/Volumes

Figure 9:
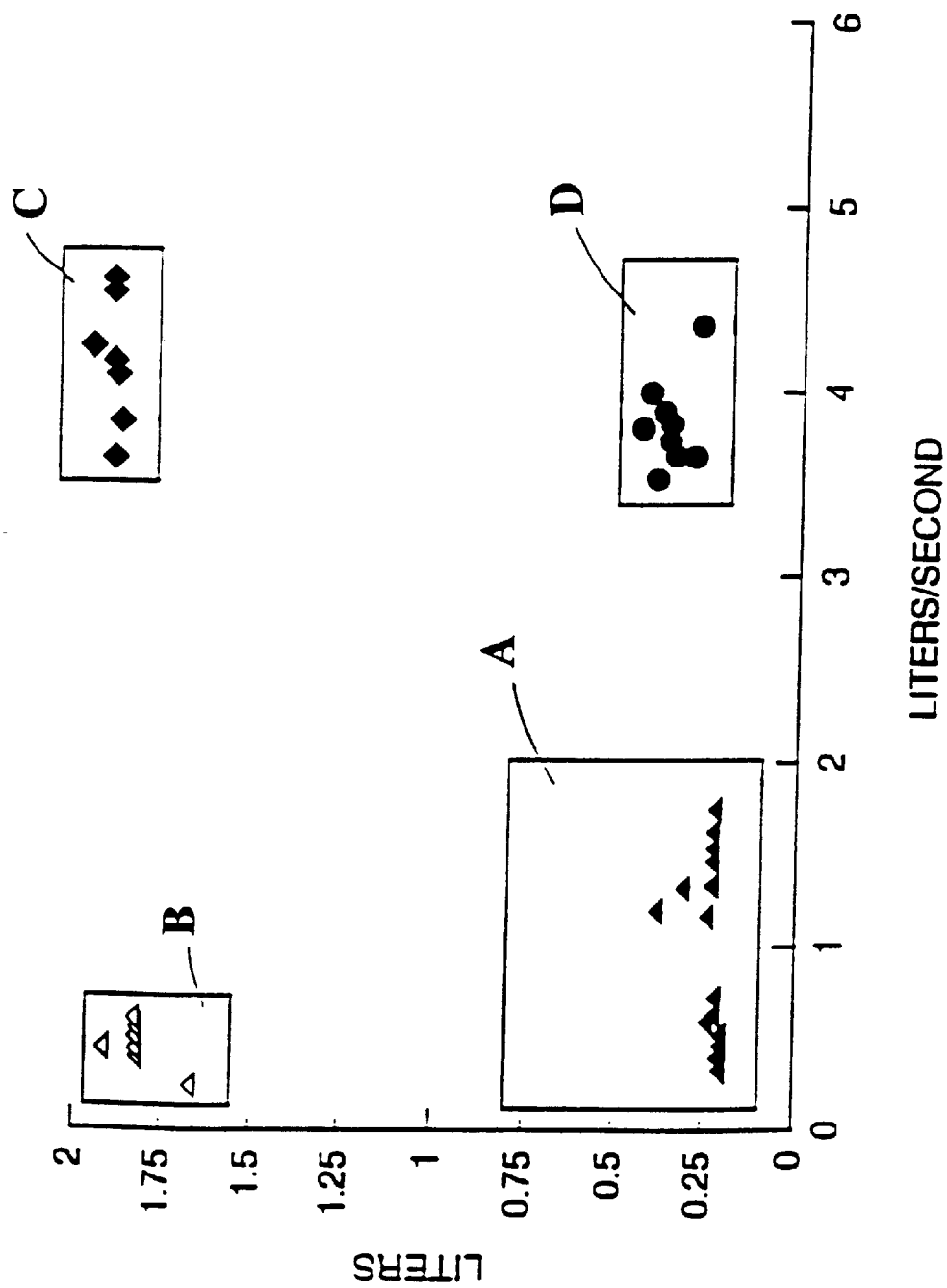
FIG. 9 is a graph showing data points plotted in four general areas with the points plotted relative to inspiratory flow rate (on the abscissa) and inspiratory volume (on the ordinate) in two dimensions.

FIG. 9 is a two-dimensional graph wherein the inspiratory flow rate is plotted against the inspiratory volume. The patient's inspiratory flow rate and inspiratory volume are simultaneously and separately measured. The measurement is taken and the information obtained from the measurement provided to a microprocessor which microprocessor is programmed to release drug (1) at the same point relative to inspiratory flow and inspiratory volume at each release of drug and (2) to select that point within prescribed parameters of inspiratory flow rates and inspiratory volumes. In the particular results plotted in FIG. 9 the microprocessor was programmed to release drug in four general areas with respect to the inspiratory flow rate and inspiratory volume parameters. This resulted in data points being plotted in four general areas on the two-dimensional graph of FIG. 9. The four areas are labeled A, B, C and D. In area A (showing solid triangles), the drug was released when the patient's inspiratory flow rate was "slow to medium" (0.10 to 2.0 liters per sec) with an "early" inspiratory volume of 0.15 to 0.8 liters. In area B (showing open triangles), the drug was released at a "slow" inspiratory rate/0.10 to 1.0 liters/sec) and a "late" volume (1.6 to 2.8 liters). In area C (showing solid diamonds), the drug was released at a "fast" inspiratory flow rate (3.5 to 4.5 liters/sec) and a "late" volume. In area D (showing solid circles), the drug was released at a "fast" inspiratory flow rate and an "early" inspiratory volume.

The results shown in FIG. 9 were obtained while administering a radioactively labeled drug to a human. After the administration of the drug it was possible to determine not only the amount of drug, but the pattern of drug deposited within the lungs of the patient. Using this information two conclusions were reached. Firstly, it was determined that it is important to simultaneously and separately consider (in real time) both inspiratory flow rate and inspiratory volume when determining the point for drug release for intrapulmonary drug delivery. Changes in either parameter can greatly effect the amount of drug deposited. Thus, when treating a patient the drug should be released at approximately (±10%, preferably ±5% and most preferably as close as possible to the first release point) the same inspiratory flow rate and inspiratory volume each time—going back to the same point each time for the same patient ensures repeatable dosing. In practice the tighter the point is defined the greater the repeatability of dosing. However, if the point is defined to precisely it can be difficult for the patient to obtain that rate/volume point again. Thus, some degree of tolerance is generally applied. Secondly, it was found that within particular ranges with respect to inspiratory flow rate and inspiratory volume it was possible to obtain a consistently high percentage amount of drug deposited in the lung. Such results are shown graphically within the three dimensional graph as shown in FIG. 10.

Figure 10:
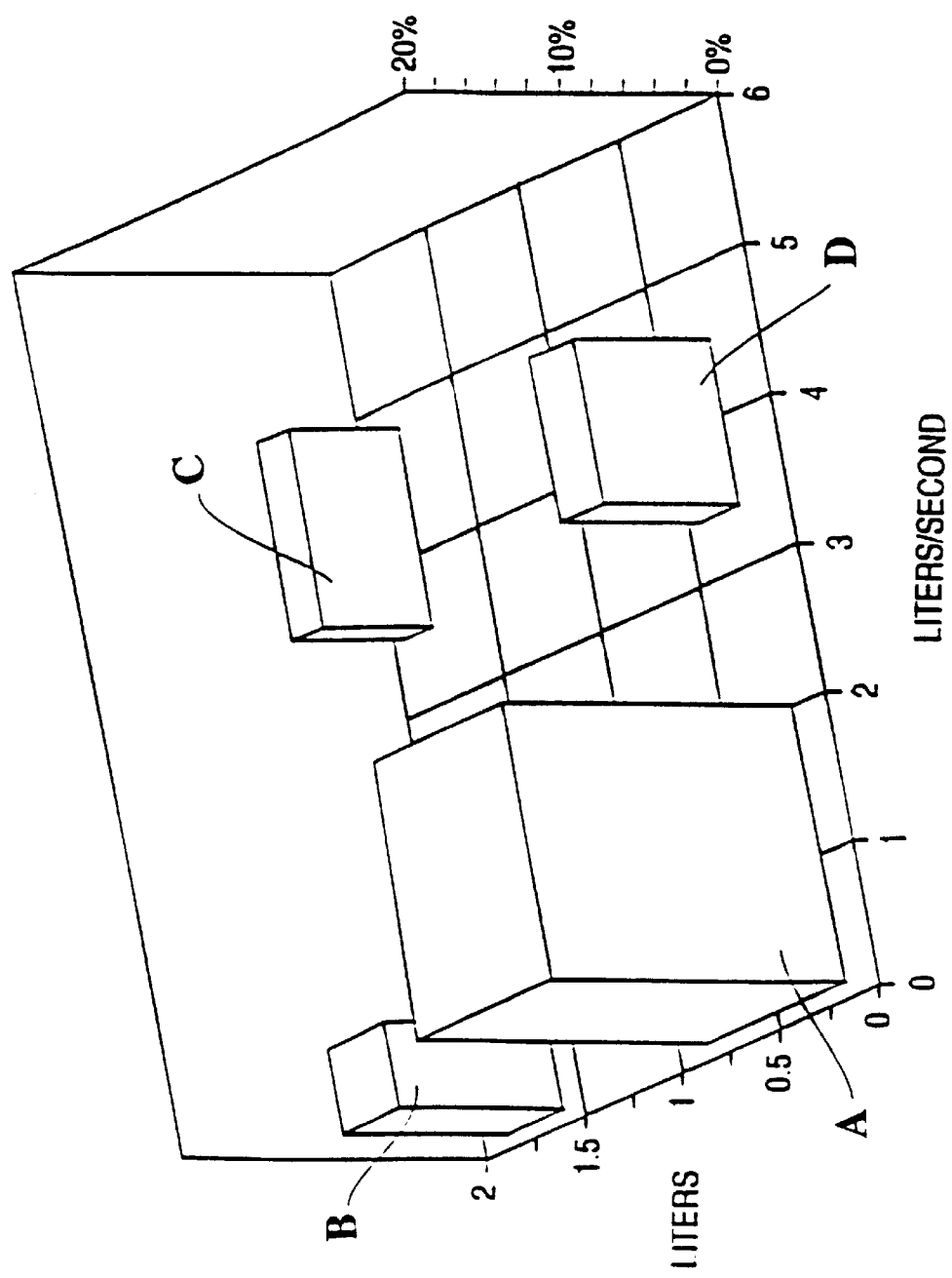
FIG. 10 is a graph showing the four general areas plotted per FIG. 1 now plotted with a third dimension to show the percentage of drug reaching the lungs based on a constant amount of drug released.

The third dimension as shown in FIG. 10 (the height of the four columns) indicates the percentage amount of drug deposited based on the total amount of drug released to the patient. The area labeled A clearly showed the highest percentage of drug delivered to the patient based on the amount of drug released. Using this information it was possible to calculate a specific area regarding inspiratory flow rate and inspiratory volume at which it is possible to obtain not only a high degree of repeatability in dosing, but obtain a higher percentage of drug being delivered based on the percentage of drug released. Specifically, it was determined that the drug should be released within an inspiratory flow rate range of 0.10 to 2.0 liters per second and at an inspiratory volume in the range of about 0.15 to about 0.80 liters. This range is shown by the rectangularly shaped column of FIG. 11.

In that intrapulmonary drug delivery systems often provide for erratic dosing it is important to provide a method which allows for consistent, repeatable dosing. This is obtained by simultaneously and separately considering both inspiratory flow rate and inspiratory volume in order to determine a point by its abscissa and ordinate. If both measurements are separately considered the drug can be released anywhere along the abscissa and ordinate scales shown in FIG. 9. Once a point is selected (such as by randomly selecting a point in box A of the graph of FIG. 9) that selected point (with the same coordinants) is used again and again by a given patient to obtain repeatable dosing. If only one parameter is measured (abscissa or ordinate) and drug is released based on that parameter the drug release point is defined by a line on the graph of FIG. 9. When drug is released again the release can be at any point on that line. For example, the inspiratory flow rate (measured horizontally on the abscissa) might be defined by a point. However, the inspiratory volume (which was not measured and/or considered) would be defined only by a vertical line. Thus, subsequent releases would be at different volumes along that vertical line and the dosing would not be consistent. By measuring both inspiratory flow rate on the abscissa and inspiratory volume on the ordinant the coordinants will mark a point for drug release. That point can be found again and again to obtain repeatability in dosing. The same point should be selected each time as closely as possible and within a margin of errors of ±10% with respect to each criteria. The margin for error can be increased and still maintain acceptable levels of repeatable dosing—but the error should keep the drug release point inside the box A of FIG. 9.

Figure 11:
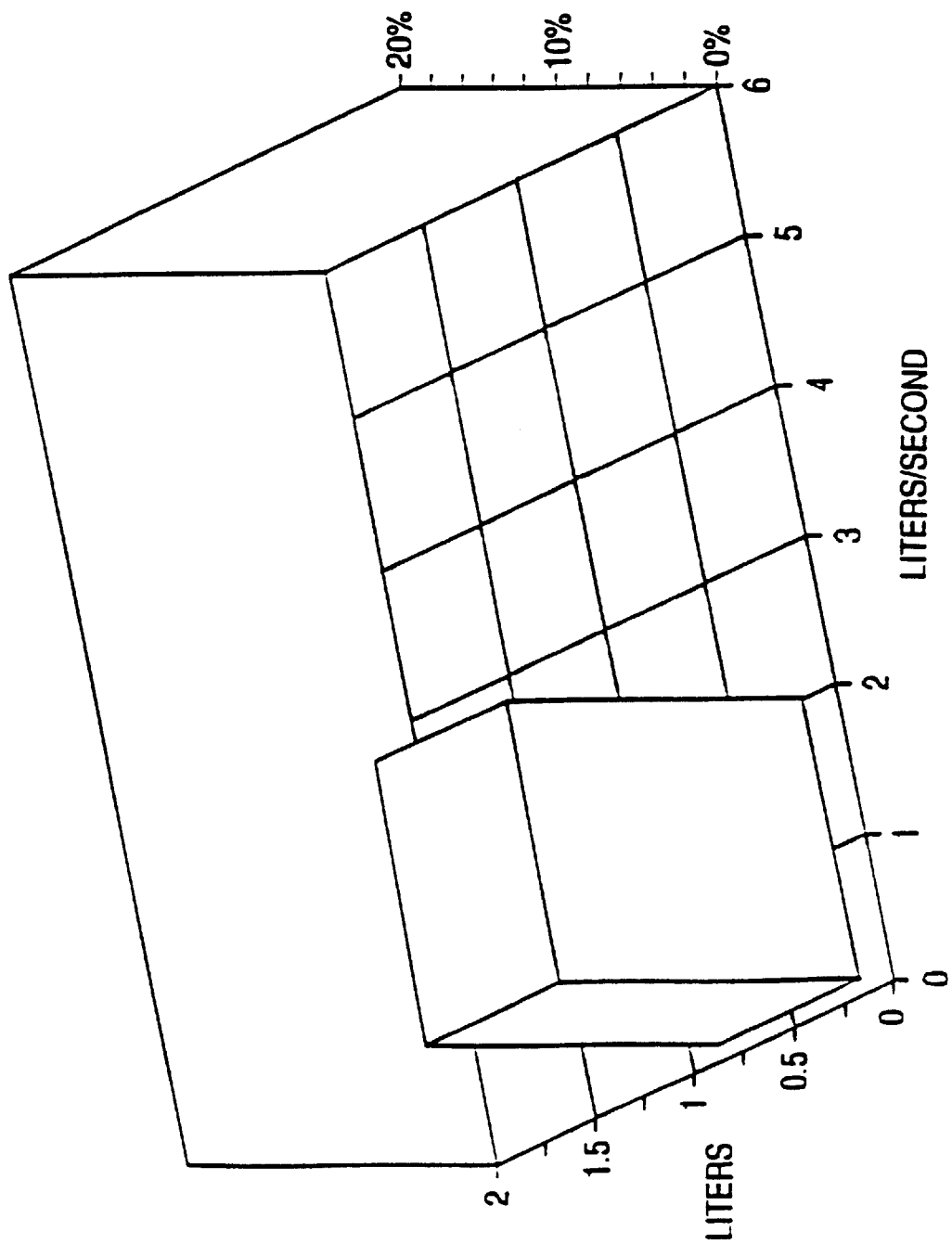
FIG. 11 is a three dimensional graph showing the therapeutic values for inspiratory flow rate and inspiratory volume which provide better drug delivery efficiency.
Figure 12:
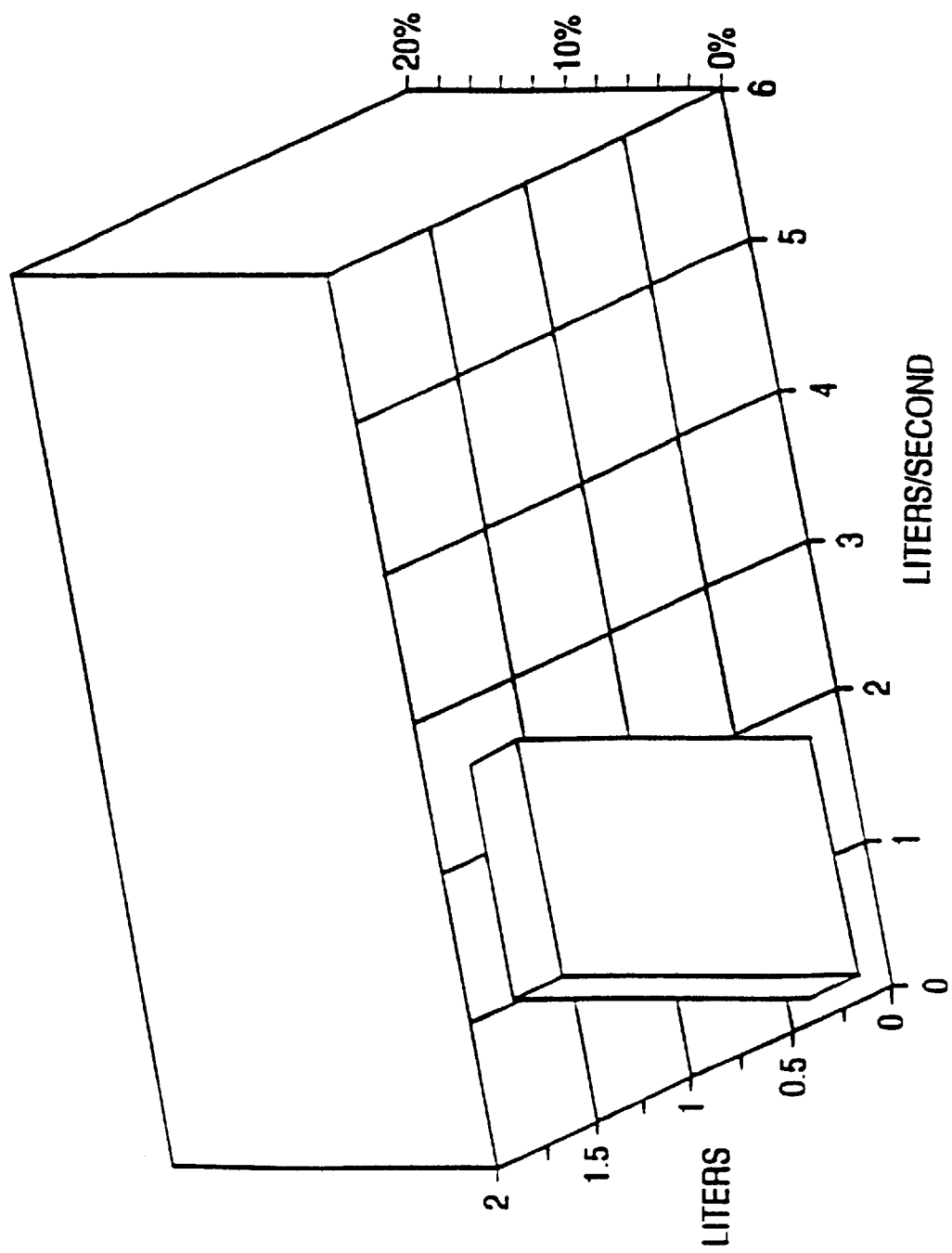
FIG. 12 shows a preferred range of the valves shown in FIG. 11.
Figure 13:
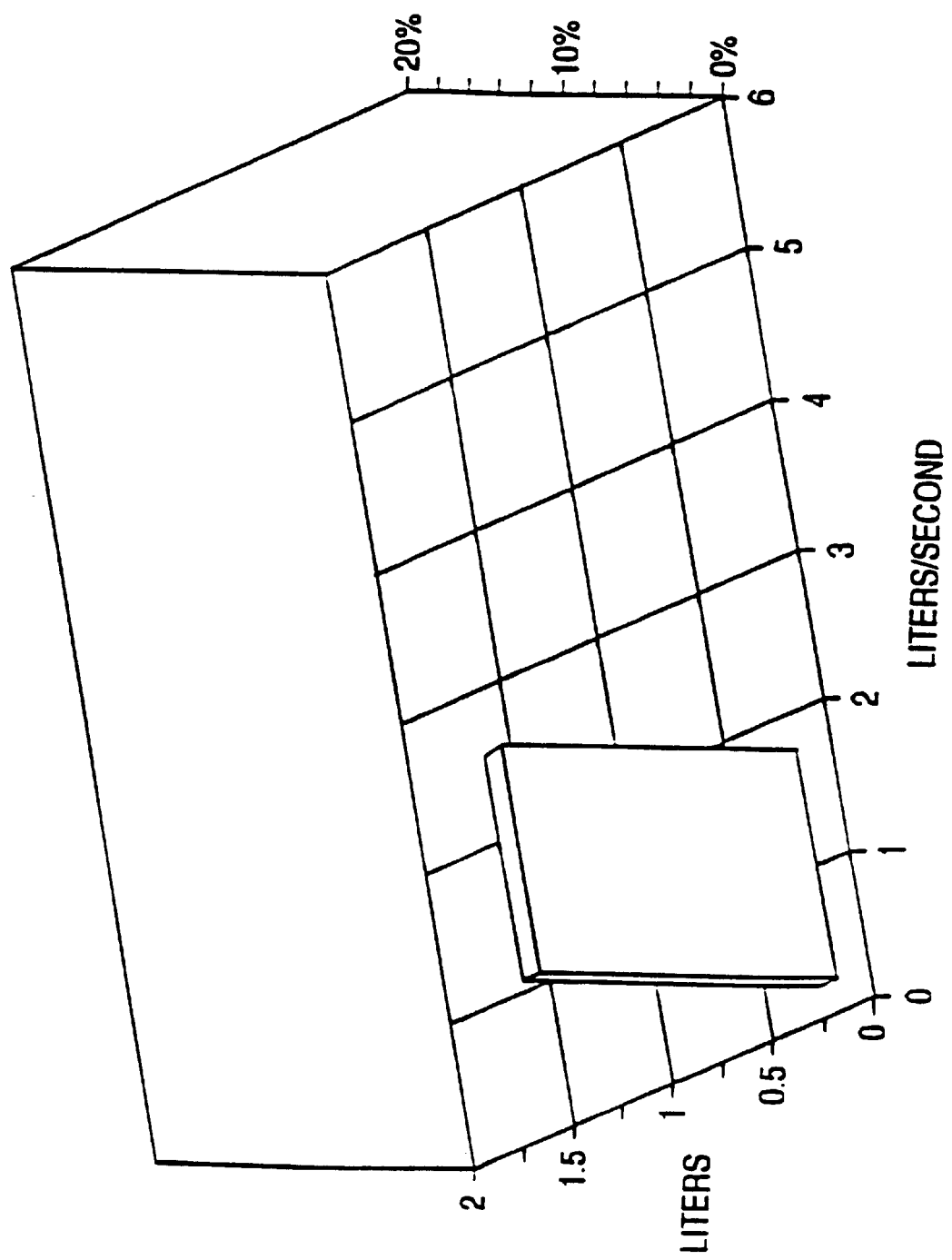
FIG. 13 shows a particularly preferred range for the valves of FIG. 11.

By examining delivery of drug associated with the data points plotted in FIG. 9, it is possible to determine a preferred and particularly preferred and most preferred range as per FIGS. 11, 12 and 13. The preferred range of FIG. 11 shows drug released at a volume of 0.15 to 0.8 liters and rate of 0.10 to 2.0 liters/second. The particularly preferred range plotted in FIG. 12 indicates that the inspiratory flow should be within the range of 0.2 to about 1.8 liters per second with an inspiratory volume in the range of 0.15 to about 0.4 liters. The most preferred range (FIG. 13) is from about 0.15 to about 1.8 liters per second for the inspiratory flow rate and about 0.15 to about 0.25 liters for the inspiratory volume. Thus, preferred delivery can be obtained by (1) repeatedly delivering aerosolized formulation to a patient at the same simultaneously and separately measured inspiratory flow rate and inspiratory volume and (2) releasing drug to the patient within specified therapeutically effective ranges as shown within FIGS. 11, 12 and 13. The invention involves releasing drug (after measuring) inside the ranges as per FIGS. 11, 12 or 13. Thus, the release could begin inside or outside the range. Preferably the drug release begins inside the range and more preferable begins and ends inside the ranges of FIGS. 11, 12 or 13.

The methodology of the invention may be carried out using a portable, hand-held, battery-powered device which uses a microprocessor as per U.S. Pat. Nos. 5,404,871, issued Apr. 11, 1995 and 5,450,336, issued Sep. 12, 1995 incorporated herein by reference. In accordance with another system the methodology of the invention could be carried out using the device, dosage units and system disclosed in US94/05825 with modifications as described herein. Respiratory drug is included in an aqueous formulation which is aerosolized by moving the formulation through a flexible porous membrane. Alternatively, the methodology of the invention could be carried out using a mechanical (non-electronic) device. Those skilled in the art would recognize that various components can be mechanical set to actuate at a given inspiratory flow rate (e.g. a spring biased valve) and at a given volume (e.g. a spinable flywheel which rotates a given amount per a given volume). The components of such devices could be set to allow drug release inside the parameters of FIGS. 11, 12 or 13.

The respiratory drug which is released to the patient may be in a variety of different forms. For example, the drug may be an aqueous solution of drug, i.e., drug dissolved in water and formed into small particles to create an aerosol which is delivered to the patient. Alternatively, the drug may be in a solution wherein a low-boiling point propellant is used as a solvent. In yet, another embodiment the drug may be in the form of a dry powder which is intermixed with an airflow in order to provide for particlized delivery of drug to the patient.

Regardless of the type of drug or the form of the drug formulation, it is preferable to create drug particles having a size in the range of about 0.5 to 9 microns. The size can be adjusted to direct the drug to a particular area of the lung which needs treatment. By creating drug particles which have a relatively narrow range of size, it is possible to further increase the efficiency of the drug delivery system and improve the repeatability of the dosing. Thus, it is preferable that the particles not only have a size in the range of 0.5 to 9 microns but that the mean particle size be within a narrow range so that 80% or more of the particles being delivered to a patient have a particle diameter which is within ±20%. of the average particle size, preferably ±10% and more preferably ±5% of the average particle size.

The velocity at which the aerosolized drug is released to the patient is also important in terms of obtaining a high degree of repeatability in dosing and providing for a high percentage of drug being delivered to the patient's lungs. Most preferably, the drug is released from a container in a direction which is normal to the patient's airflow. Accordingly, the drug may be released directly upward so that its flow is at a 90° angle with respect to the patient's inspiratory flow which is directly horizontal. After being released, the drug velocity decreases and the drug particles remain suspended for a sufficient period of time to allow the patient's inspiration to draw the drug into the patient's lungs. The velocity of drug released in the direction from the drug release point to the patient may match the patient's inspiratory flow rate but is preferably slower that the patient's inspiratory flow rate and is most preferably about zero. The velocity may be slightly negative, i.e., in a direction away from the patient. The velocity may range from −2.0 liters/sec to 2.0 liters/sec and is preferably zero. It is not desirable to project the drug toward the patient at a rate above the speed of the patient's breath as such may result in drug being deposited on the back of the patient's throat. Thus, the drug release speed should be equal to or less than the breath speed. The actual speed of release can vary depending on factors such as the particle size, the particle composition and the distance between the point of release and the patient. The velocity is preferably such that the particles will (due to air resistance) slow to zero velocity after traveling a distance of about 2 centimeters or less. In general, the shorter the distance required to slow the particles to zero velocity the better.

An aerosol may be created by forcing drug through pores of a membrane which pores have a size in the range of about 0.25 to 6.0 microns, preferably 2.0 to 7.0 microns and more preferably 2.0 to 5.0 microns. When the pores have this size the particles which escape through the pores to create the aerosol will have a diameter about twice the diameter of the pore size. However, the particle size can be substantially reduced by adding heat to evaporate carrier. Drug particles may be released with an air flow intended to keep the particles within this size range. The creation of small particles may be facilitated by the use of the vibration device which provides a vibration frequency in the range of about 800 to about 4000 kilohertz. Those skilled in the art will recognize that some adjustments can be made in the parameters such as the size of the pores from which drug is released, vibration frequency, pressure, and other parameters based on the density and viscosity of the formulation keeping in mind that the object is to provide aerosolized particles having a diameter in the range of about 0.5 to 9 microns.

The drug formulation may be a low viscosity liquid formulation. The viscosity of the drug by itself or in combination with a carrier is not of particular importance except to note that the formulation must have characteristics such that the formulation can be forced out of openings to form an aerosol, e.g., when the formulation is forced through the flexible porous membrane it will form an aerosol preferably having a particle size in the range of about 0.5 to 9 microns.
Particle Size Adjustment.

One aspect of the invention involves manipulating the particle sizes in order to treat particular areas of the lung. For example, when it is desirable to treat the outer most peripheral areas of the lung the method of the present invention involves reducing the particle size to a particle size in the range of 0.5 to 3 microns. When it is desirable to treat the more central areas of the lung larger particle sizes are used and the particle size is adjusted to a size in the range of 5 to 9 microns. In some instances it is desirable to treat both areas simultaneously and to deliver aerosolized drug wherein the particle size is distributed over two different ranges. For example, the particle size could be distributed closely to a size of about 2 microns (within the range of 0.5 to 3 microns) for one group of particles and distributed close to a particle size of about 7 microns (within the range of 5 to 9 microns). The smaller particles would reach and treat, primarily, the peripheral areas of the lungs whereas the larger particles would reach and primarily treat the central areas of the lungs. In some instances, the particle size distribution is kept relatively broad over a range of 0.5 to 9 microns.
Dynamic Particle Size Adjustment.

Different types of drug delivery devices which can be used in connection with the methodology of the invention are described in detail below and with reference to the attached figures. All of the devices create an aerosolized form of a drug containing formulation which the patient inhales into the lungs. From the period of time from the formation of the aerosolized particles until the particles actually contact the lung surface, the size of the particles is subject to change due to increases or decrease in the amount of water in the formulation due to the relative humidity within the surrounding atmosphere. More specifically, water vapor present in the surrounding atmosphere contacts the particles which absorb the water and grow in size. Alternatively, in a particularly dry atmosphere, water is drawn away from the particles and they are reduced in size. In order to obtain consistency in terms of the size of particles delivered to the patient regardless of the surrounding atmosphere, it is desirable to include a component within the drug delivery device which adds energy to the surrounding atmosphere (heats the atmosphere) and thereby minimizes the effect of high humidity conditions and reduces the particle size to a minimum consistent size. Alternatively, water vapor could be added to the surrounding atmosphere of the aerosol so that the particles would always enlarge to a maximum consistent size. Detailed information on dynamic particle size adjustment is contained within U.S. Patent application entitled "Dynamic Particle Size Reduction for Aerosolized Drug Delivery", U.S. patent application Ser. No. 08/313,461 filed Sep. 27, 1994, which application is incorporated herein by reference in its entirety and specifically incorporated in order to disclose and describe components used in particle size adjustment by the addition of heat to air surrounding the particles.
Drug Formulation Containers.

Drug may be stored in and/or released from a container of any desired size. In most cases the size of the container is not directly related to the amount of drug being delivered in that most formulations include relatively large amounts of excipient material e.g. alcohol, (e.g., ethanol with or without water) water or a saline solution. Accordingly, a given size container could include a wide range of different doses by varying drug concentration.

The amount of respiratory drug delivered to the patient will vary greatly depending on the particular drug being delivered. In accordance with the present invention it is possible to deliver a wide range of respiratory drugs. For example, drugs included within the container could be anti-inflammatory drugs, bronchodilators, enzymes, steroid or anticholenergics.

Drug containers may include indices which may be electronic and may be connected to a power source such as a battery. When the indices are in the form of visually perceivable numbers, letters or any type of symbol capable of conveying information to the patient. Alternatively, the indices may be connected to a power source such as a battery when the indices are in the form of magnetically, optically or electronically recorded information which can be read by a drug dispensing device which in turn provides visual or audio information to the user. The indices can be designed for any desired purpose but in general provides specific information relating to the day and/or time which the drug within a container should be administered to the patient. Such indices may record, store and transfer information to a drug dispensing device regarding the number of doses remaining in the container. The containers may include labeling which can be in any format and could include days of the month or other symbols or numbers in any variation or language.

In addition to disclosing specific information regarding the day and time for drug delivery the indices could provide more detailed information such as the amount of drug dispensed from each container which might be particularly useful if the containers included different amounts of drug. Further, magnetic, optical and/or electronic indices could have new information recorded onto them which information could be placed there by the drug dispensing device. For example, a magnetic recording means could receive information from the drug dispensing device indicating the precise time which the drug was actually administered to the patient. In addition to recording the time of delivery the device could monitor the expected efficacy of the delivery based on factors such as the inspiratory flow rate which occurs following the initial release of drug. The information recorded could then be read by a separate device, interpreted by the care-giver and used to determine the usefulness of the present treatment methodology. For example, if the patient did not appear to be responding well but the recorded information indicating that the patient had taken the drug at the wrong time or that the patient had misdelivered drug by changing inspiratory flow rate after initial release it might be determined that further education in patient use of the device was needed but that the present dosing methodology might well be useful. However, if the recordings indicate that the patient had delivered the drug using the proper techniques and still not obtained the correct results a different drug or dosing methodology might be recommended.

Figure 7:
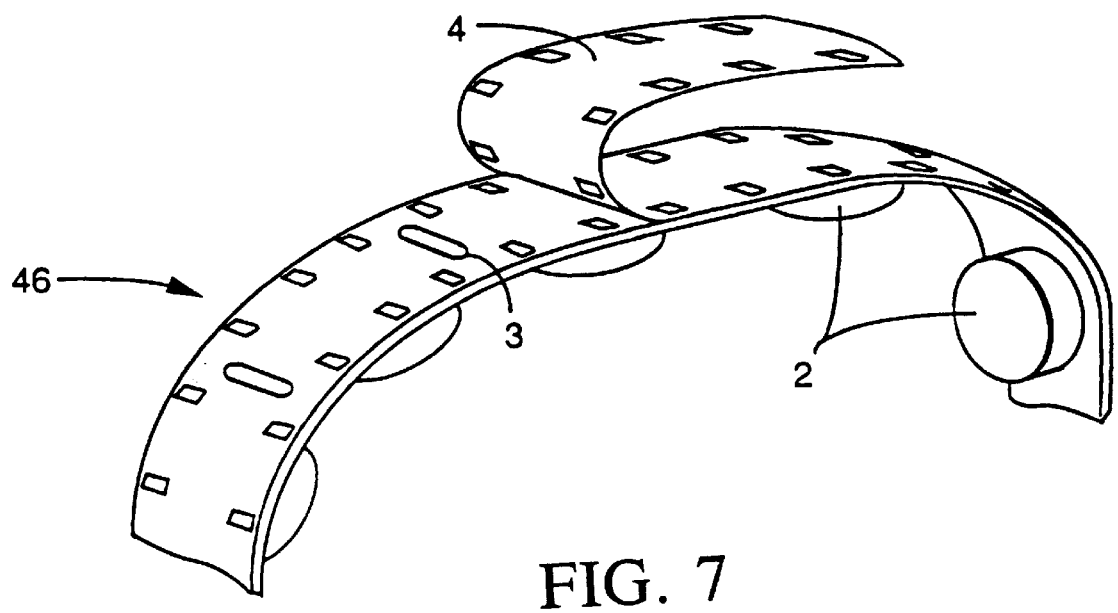
FIG. 7 is a perspective view of the package of the invention.
Figure 8:
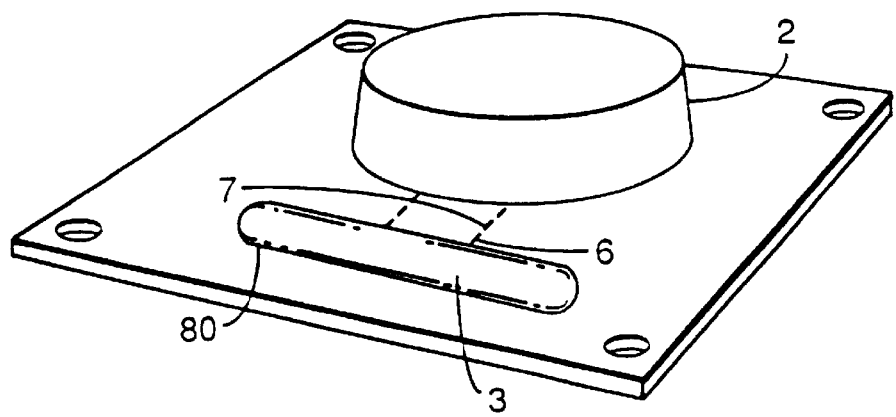
FIG. 8 is a perspective view of a container of the invention.

As shown in FIG. 3 the convex shape that the flexible membrane 3 takes on during use plays an important role at this point. The membrane may be rigid and convex and a rigid convex membrane 80 is shown in FIG. 8. Alternatively, formulation 5 is forced from the container 1 by force applied from a source such as the piston or plate 24 causing the formulation 5 to press against a flexible membrane 3 causing it to convex outward beyond the plane of the resting surface of the membrane 3 and beyond the plane of the inner surface of the channel 11 which is aligned with the surface or membrane 3 when the container 1 is in a drug release position. The convex shape of the membrane 3 is shown in FIG. 3. The convex upward distortion of the membrane is important because it positions the pores of the membrane beyond the boundary layer 13 (shown in FIG. 3) into faster moving air of the channel 29. A number of containers may be connected together to form a package 46 as is shown in FIG. 7. The package 8 is in the form of an elongated tape but can be in any configuration, e.g., circular, square, rectangular, etc.

When pores of the membrane 3 are positioned beyond the boundary layer into the faster moving air of the channel advantages are obtained. Specifically, the (1) formulation exiting the pores is moved to an air stream where it can be readily carried to the patient and (2) the particles formed do not exit into slow moving or "dead" air and thus do not rapidly decelerate to a degree such that particles behind them catch up with, collide into and merge with the particle. Particle collisions are not desirable because they (a) result in particles which are too large and cannot be efficiently inhaled into the lung; and (b) result in an aerosol with diverse and unpredictable particle sizes. Either or both (a) and (b) can result in erratic dosing.

The air-heating mechanism 14 heats the surrounding air within the flow path 29. This causes carrier in the formulation to be evaporated more readily. If sufficient heat is added the only material reaching the patient is the substantially dry powder drug.

The methodology of the present invention could be carried out with a device that obtains power from a plug-in source. However, the device is preferably a self-contained, hand-held device which is battery powered. Heating mechanisms of various types can be used. For example, see the heating mechanism in the self-contained, portable sealer for plastic colostomy bags in French patent 2,673,142 which is incorporated herein by reference. A portable heater is also taught in European patent applications 0,430,566 A2 for a "Flavor delivering article" and 0,358,002 for "Smoking articles utilizing electric energy," both of which are incorporated herein by reference to disclose and describe heating components powered by batteries.

Method of Treatment

The method of treating respiratory disease may be carried out using a hand-held, portable device comprised of (a) a device for holding a disposable package comprised of at least one but preferably a number of drug containers, (b) a propellant or a mechanical mechanism for moving the contents of a container through a porous membrane (c) a monitor for analyzing the inspiratory flow, rate and volume of a patient, and (d) a switch for (preferably automatically) releasing or firing the mechanical means (preferably) after the inspiratory flow and/or volume reaches a threshold level. The device may also include a transport mechanism to move the package from one container to the next. The entire device is self-contained, light weight (less than 1 kg preferably less than 0.5 kg loaded) and portable.

The device may include a mouth piece at the end of the flow path, and the patient inhales from the mouth piece which causes an inspiratory flow to be measured within the flow path which path may be in a non-linear flow-pressure relationship. This inspiratory flow causes an air flow transducer to generate a signal. This signal is conveyed to a microprocessor which is able to convert, continuously, the signal from the transducer in the inspiratory flow path to a flow rate in liters per minute. The microprocessor can further integrate this continuous air flow rate signal into a representation of cumulative inspiratory volume. At an appropriate point in the inspiratory cycle, the microprocessor can send a signal to an actuation means (and/or a vibration device below the resonance cavity). When the actuation means is signaled, it causes the mechanical means (by pressure or vibration) to move drug from a container on the package into the inspiratory flow path of the device and ultimately into the patient's lungs. After being released, the drug and carrier will pass through a porous membrane which is vibrated to aerosolize the formulation and thereafter the lungs of the patient. Containers and systems of the type described above are disclosed and described in U.S. patent application Ser. No. 08/247,012 filed May 20, 1994 which is incorporated herein by reference to disclose and describe such containers and systems.

Humidity Control via Desiccator

When the formulation 5 includes water as all or part of the carrier it is also desirable to include a desiccator 41 within the flow path 29. The desiccator 41 is preferably located at the initial opening 38 but maybe located elsewhere in the flow path 29 prior to a point in the flow path when the formulation is fired into the flow path in the form of aerosolized particles. By drawing air through the desiccator 41 water vapor within the air is removed in part or completely. Therefore, only dried air is drawn into the remainder of a flow path. Since the air is completely dried water carrier within the aerosolized particles will more readily evaporate. This decreases the energy needs with respect to the heating devices 14. The desiccator material can be any compound which absorbs water vapor from air. For example, it may be a compound selected from the group consisting of $P_2O_5$, $Mg(ClO_4)$, KOH, $H_2SO_4$, NaOH, CaO, $CaCl_2$, $ZnCl_2$, and $CaSO_4$.

Firing Point

It is important to note that the firing threshold of the device is preferably not based on a single criterion such as the rate of air flow through the device or a specific time after the patient begins inhalation. The firing threshold is based on an analysis of the patient's inspiratory flow profile. This means that the microprocessor controlling the device takes into consideration the instantaneous air flow rate as well as the cumulative inspiratory flow volume. Both are simultaneously considered together in order to determine the optimal point in the patient's inspiratory cycle most preferable in terms of reproducibly delivering the same amount of drug to the patient with each release of drug.

Drug Delivery Device

The device preferably includes a means for recording a characterization of the inspiratory flow profile for the patient which is possible by including a microprocessor 26 in combination with a read/write memory means and a flow measurement transducer. By using such devices, it is possible to change the firing threshold at any time in response to an analysis of the patient's inspiratory flow profile, and it is also possible to record drug dosing events over time. In a particularly preferred embodiment the characterization of the inspiratory flow can be recorded onto a recording means on the disposable package.

Figure 4:
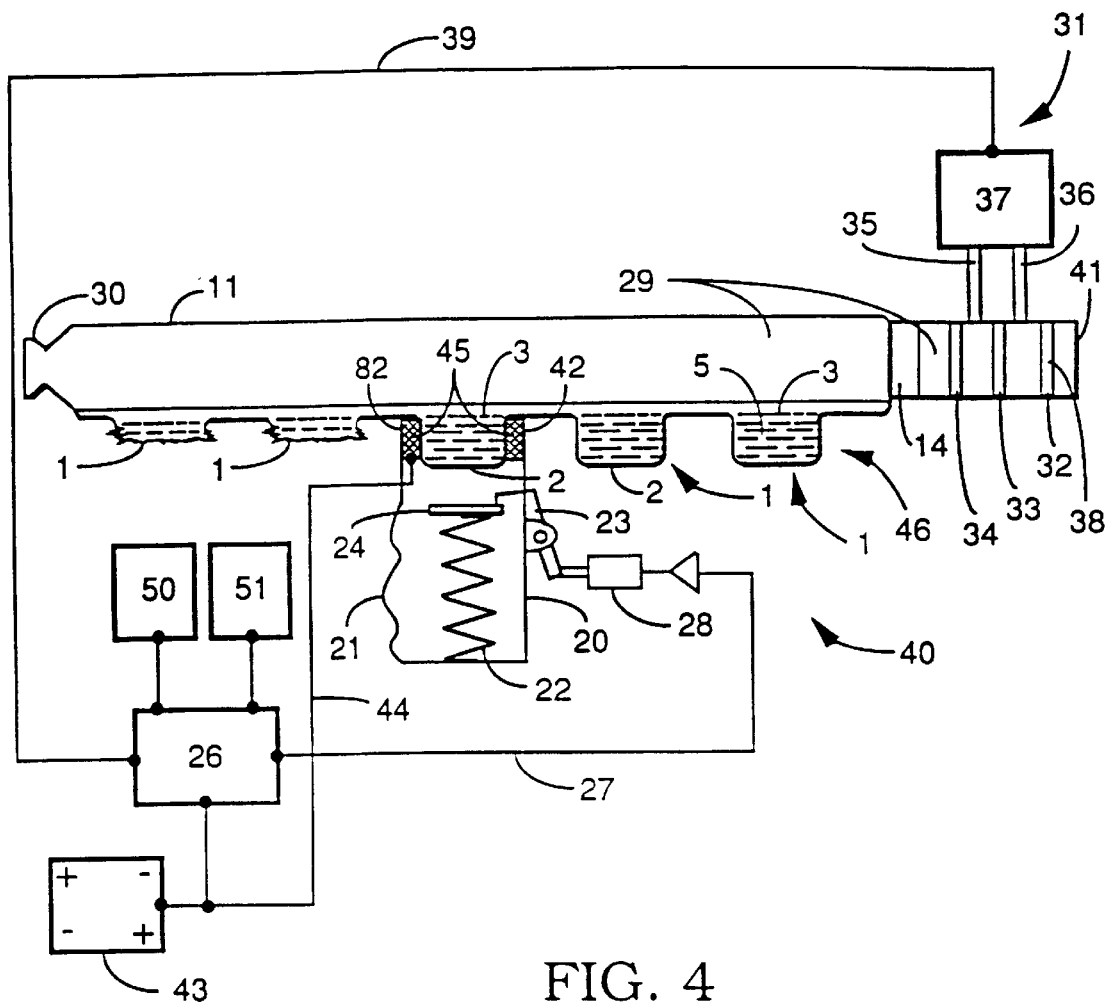
FIG. 4 is a plan view of a drug delivery device of the invention.

FIG. 4 shows a cross-sectional plan view of a hand held, self-contained, portable, breath-actuated inhaler device 40 of the present invention. The device 40 is shown with a holder 20 having cylindrical side walls and a hand grip 21. The holder 20 is "loaded" in that it includes a container 1. A plurality of containers 1 (2 or more) are preferably linked together to form a package 46.

The embodiment shown in FIG. 4 is a simple version of the invention. The device 40 may be manually actuated and loaded. More specifically, the spring 22 may be compressed by the user until it is forced down below the actuation mechanism 23. When the user pushes the actuation mechanism 23 the spring 22 is released and the mechanical means in the form of a plate 24 is forced upward against a wall 2 of a container 1. When the container 1 is compressed its contents are forced out through the membrane 3 and aerosolized. Two additional containers 1 shown to the left is unused. The device of FIG. 4 would not require the use of low boiling point propellants such as low boiling point fluorocarbons. Numerous additional features and advantages of the present invention can be obtained by utilizing the monitoring and electronic components described below.

It is important to note that a variety of devices can be used in order to carry out the methodology (including the respiratory disease treatment methodology) of the present invention. However, the device must be capable of aerosolizing drug formulation in a container and preferably does such forcing formulation through a porous membrane with the release point based on pre-programmed criteria which may be mechanically set or electronically set via criteria readable by the microprocessor 26. The details of the microprocessor 26 and the details of other drug delivery devices which include a microprocessor and pressure transducer of the type used in connection with the present invention are described and disclosed within U.S. Pat. No. 5,404,871, issued Apr. 11, 1995, entitled "Delivery of Aerosol Medications for Inspiration" which patent is incorporated in its entirety herein by reference, and it is specifically incorporated in order to describe and disclose the microprocessor and program technology used therewith. The use of such a microprocessor with a drug delivery device is disclosed in our earlier filed U.S. application Ser. No. 08/065,660 filed May 21, 1993 incorporated herein by reference. The pre-programmed information is contained within a nonvolatile memory which can be modified via an external device. In another embodiment, this pre-programmed information is contained within a "read only" memory which can be unplugged from the device and replaced with another memory unit containing different programming information. In yet another embodiment, microprocessor 26, containing read only memory which in turn contains the pre-programmed information, is plugged into the device. For each of these three embodiments, changing the programming of the memory device readable by microprocessor 26 will radically change the behavior of the device by causing microprocessor 26 to be programmed in a different manner. This is done to accommodate different drugs for different types of treatment.

Microprocessor 26 sends signals via electrical connection 27 to electrical actuation device 28 which actuates the means 23 which fires the mechanical plate 24 forcing drug formulation in a container 1 to be aerosolized so that an amount of aerosolized drug is delivered into the inspiratory flow path 29 when the flexible membrane 3 protrudes outward through the flow boundary layer. A signal is also sent to the heater 14 to add heat energy to the air in the flow path 29. The device 28 can be a solenoid, motor, or any device for converting electrical to mechanical energy. Further, microprocessor 26 keeps a record of all drug dosing times and amounts using a read/write non-volatile memory which is in turn readable by an external device. Alternatively, the device records the information onto an electronic or magnetic strip on the package 1. The recorded information can be read later by the care-giver to determine the effectiveness of the treatment. In order to allow for ease of use, it is possible to surround the inspiratory flow path 29 with a mouth piece 30.

The electrical actuation means 28 is in electrical connection with the flow sensor 31 which is capable of measuring a flow rate of about 0 to about 800 liters per minute. It should be noted that inhalation flow rates are less than exhalation rates, e.g. max for inhalation 200 1pm and 800 1pm for exhalation. A variety of different types of flow sensors may be used as per U.S. Pat. No. 5,394,866, issued Mar. 7, 1995, U.S. Pat. No. 5,404,871, issued Apr. 11, 1995 and U.S. Pat. No. 5,450,336, issued Sep. 12, 1995, which are incorporated herein by reference. The flow sensor 31 includes screens 32, 33 and 34 which are positioned approximately ¼" apart from each other but may be comprised of a single screen or include a non-linear flow path. It is preferable to include the desiccator 41 at a point prior to the screens 32, 33 and 34 in the flow path so that the elimination of water vapor is considered in any measurement.

Tubes 35 and 36 open to the area between the screens 32, 33 and 34 with the tubes 35 and 36 being connected to a conventional differential pressure transducer 37. Another transducer designed to measure outflow through the opening 38 is also preferably included or the flow sensor 31 is designed so that the same components can measure inflow and outflow. When the user draws air through inspiratory flow path 29, air is passed through the screens 32, 33 and 34 and the air flow can be measured by the differential air pressure transducer 37. Alternatively, other means to measure pressure differential related to air flow, such as a conventional measuring device in the air way, may be used. The flow sensor 31 is in connection with the electrical actuation means 28 (via the connector 39 to the processor 26), and when a threshold value of air flow is reached (as determined by the processor 26), the electrical actuation means 28 fires the release of a mechanical means 23 releasing the plate 24 which forces the release of formulation from a container 1 so that a controlled amount of respiratory drug is delivered to the patient. The microprocessor 26 is optionally connected to an optionally present vibrating device 45 which may be activated.

Vibration Device

The vibration device 45 creates ultrasonic vibrations which are preferably at right angles to the plane of the membrane 3. The device 45 may be in the form of a piezoelectric ceramic crystal or other suitable vibration mechanism. A vibrating device 45 in the form of a piezoelectric crystal may be connected to the porous membrane by means of an attenuator horn or acoustic conduction mechanism, which when correctly matched with the piezoelectric crystal frequency, efficiently transmits ultrasonic oscillations of the piezoelectric crystal to the resonance cavity and the porous polycarbonate membrane and if sized correctly permits the ultrasonic energy to be focused in a polycarbonate membrane 3 allowing for maximum use of the energy towards aerosolizing the liquid formulation 5. The size and shape of the attenuator horn is not of particular importance. It is preferred to maintain a relatively small size in that the device is hand held. The components are chosen based on the particular material used as the porous material, the particular formulation used and with consideration of the velocity of ultrasonic waves through the membrane to achieve a harmonic relationship at the frequency being used.

A high frequency signal generator drives the piezoelectric crystal. This generator is capable of producing a signal having a frequency of from about 575 kilohertz (Khz) to about 32,000 kilohertz. The power output required depends upon the amount of liquid being nebulized per unit of time and the area and porosity of the membrane (generally comprised of a polymeric plastic-like material) used for producing the drug dosage unit and/or the efficiency of the connection.

Vibration is applied while the formulation 5 is being forced from the pores of the polycarbonate membrane 3. The formulation can be aerosolized with only vibration i.e., without applying pressure. Alternatively, when vibration is applied in certain conditions the pressure required for forcing the liquid out can be varied depending on the liquid, the size of the pores and the shape of the pores but is generally in the range of about 50 to 600 psi, preferably 100 to 500 psi and may be achieved by using a piston, roller, bellows, a blast of forced compressed gas, or other suitable device. The vibration frequency used and the pressure applied can be varied depending on the viscosity of the liquid being forced out and the diameter and length of the openings or pores.

It is desirable to force formulation through the porous membrane with a relatively low pressure e.g., pressure less than 500 psi in that lower pressure reduces the chance of breaking the membrane during the release of formulation and makes it possible to make a thinner membrane. The thinner membranes make it easier to make small holes in that the holes or pores of the membrane are created using a focussed LASER. It is possible to reduce the pressure further by making the holes conical in crosssection. A LASER with a conical focus is used to burn holes through the membrane. The larger diameter of the conical shape is positioned next to the formulation and the smaller diameter opening is the opening through which the formulation ultimately flows. The ratio of the smaller opening to the diameter of the larger opening is in the range of about 1:2 to about 1:20 i.e., the larger opening is between 2 and 20 times the diameter of the smaller opening. By creating conical openings wherein the smaller end of the cone has a diameter of less than 6 microns it is possible to produce particles which have a diameter of less than 12 microns and it is also possible to force the formulation through the pores using a pressure of less than 500 psi. The small end of the conical opening preferably has a diameter of less than 3 microns for systemic delivery and less than 5 microns for pulmonary delivery and the pressure used for forcing formulation through the pores is preferably less than 350 psi.

When small aerosolized particles are forced into the air, the particles encounter substantial frictional resistance. This may cause particles to slow down more quickly than desired and may result in particles colliding into each other and combining, which is undesirable with respect to maintaining the preferred particle size distribution within the aerosol. In order to aid in avoiding the particle collision problem, it is possible to include a means by which air flow and the flexible membrane 3 prevent collisions. Specifically, the patient inhales thereby creating an air flow toward the patient over the protruding membrane 3. The air flow carries the formed particles along and aids in preventing their collision with each other. The shape of the container opening, the shape of the membrane covering that opening, as well as the positioning and angling of the flow of air through the channel 11 relative to the direction of formulation exiting the pores of the membrane 3 can be designed to aid in preventing particle collision. It is desirable to shape the opening and matching membrane so as to minimize the distance between any edge of the opening and the center of the opening. Accordingly, it is not desirable to form a circular opening which would maximize the distance between the outer edges of the circle and the center of the circle, whereas it is desirable to form an elongated narrow rectangular opening covered by a rigid membrane 80 as shown in FIG. 8. Using such a configuration makes it possible to better utilize the air flow relative to all of the particles of formulation being forced form the pores of the membrane 3. When a circular opening is used, particles which are towards the center of the circle may not be carried along by the air being drawn over the membrane 3 and will collide with each other. The elongated rectangle could be formed in a circle, thereby providing an annular opening and air could be forced outward from the outer and inner edges of the circle formed. Further details regarding such are described in U.S. patent application Ser. No. 08/247,012, filed May 20, 1994 which is incorporated herein by reference to disclose and describe such.

Operation of the Device 40

The device of FIG. 4 shows all of the components present within the single, hand-held, portable breath actuated device, e.g. the microprocessor 26 and flow sensor 31 used to provide the electronic breath actuated release of drug. The device of FIG. 4 includes a holding means and mechanical means and preferably operates electronically, i.e. the actuation means is preferably not directly released by the user. The patient inhales through inspiratory flow path 29 which can form a mouth piece 30. Air enters the device via the opening 38. The inhaling is carried out in order to obtain a metering event using the differential pressure transducer 37. Further, when the inspiratory flow meets a threshold of a pre-programmed criteria, the microprocessor 26 sends a signal to an actuator release electrical mechanism 28 which actuates the mechanical means 23, thereby releasing a spring 22 and plate 24 or equivalent thereof, forcing aerosolized formulation into the channel 11, and out of the membrane 3 into the flow path 29 where the air surrounding the particles is optionally heated by the air heater 14. Further details regarding microprocessors 26 of FIG. 4 are described within U.S. Pat. No. 5,394,866, issued Mar. 7, 1995, entitled "An Automatic Aerosol Medication Delivery System and Methods", which is incorporated herein by reference in its entirety and specifically incorporated in order to describe and disclose flow measurements, the microprocessor and program technology used therewith.

Microprocessor 26 of FIG. 4 includes an external non-volatile read/write memory subsystem, peripheral devices to support this memory system, reset circuit, a clock oscillator, a data acquisition subsystem and a visual annunciator subsystem. The discrete components are conventional parts which have input and output pins configured in a conventional manner with the connections being made in accordance with instructions provided by the device manufacturers. The microprocessor used in connection with the device of the invention is designed and programmed specifically so as to provide controlled and repeatable amounts of respiratory drug to a patient upon actuation. The microprocessor must have sufficient capacity to make calculations in real time. Adjustments can be made in the program so that when the patient's inspiratory flow profile is changed such is taken into consideration. This can be done by allowing the patient to inhale through the device as a test (monitoring event) in order to measure air flow with preferred drug delivery points determined based on the results of several inhalations by each particular patient. This process can be readily repeated when the inspiratory flow profile is changed for whatever reason. When the patient's lung function has decreased the program will automatically back down in terms of the threshold levels required for release of drug. This "back down" function insures drug delivery to a patient in need but with impaired lung function. Determination of optimal drug delivery points in the inspiratory flow can be done at each dosing event, daily, weekly, or with the replacement of a new cellular array in the device.

The microprocessor 26 of the present invention, along with its associated peripheral devices, can be programmed so as to prevent triggering the actuation mechanism 28 more than a given number of times within a given period of time. This feature makes it possible to prevent overdosing the patient. The overdose prevention feature can be particularly designed with each individual patient in mind or designed with particular groups of patients in mind. For example, the microprocessor can be programmed so as to prevent the release of more than approximately 200 μg of a given respiratory drug per day when the patient is normally dosed with approximately 100 μg of drug per day. The device can be designed to switch off this lock-out function so that drug can be delivered in an emergency situation.

The systems can also be designed so that only a given amount of a particular drug such as a respiratory drug is provided at a given dosing event. For example, the system can be designed so that only approximately 10 μg of respiratory drug is given in a given 15-minute period over which the patient will make approximately 10 inhalations with 1 μg of drug being delivered with each inhalation. By providing this feature, greater assurances are obtained with respect to delivering the respiratory drug gradually over time and thereby providing relief from the symptoms of respiratory disease without overdosing the patient.

The microprocessor 26 of the invention can be connected to external devices permitting external information to be transferred into the microprocessor of the invention and stored within the non-volatile read/write memory available to the microprocessor. The microprocessor of the invention can then change its drug delivery behavior based on this information transferred from external devices. All of the features of the invention are provided in a portable, programmable, battery-powered, hand-held device for patient use which has a size which compares favorably with existing metered dose inhaler devices.

The microprocessor 26 of the present invention is programmed so as to allow for monitoring and recording data from the inspiratory flow monitor without delivering drug. This is done in order to characterize the patient's inspiratory flow profile in a given number of monitoring events, which monitoring events preferably occur prior to dosing events. After carrying out a monitoring event, the preferred point within the inspiratory cycle for drug delivery can be calculated. This calculated point is a function of measured inspiratory flow rate as well as calculated cumulative inspiratory flow volume. This information is stored and used to allow activation of the electronic actuation means when the inhalation cycle is repeated during the dosing event.

The amount of respiratory drug delivered to the patient will vary greatly depending on the particular drug being delivered. In accordance with the present invention it is possible to deliver a wide range of different respiratory drugs with the most preferred drugs being albuterol, beclomethasone dipropionate, triamcinolone acetonide, flunisolide, cromolyn sodium, and ipratropium bromide, and include, free acids, bases, salts and various hydrate forms thereof generally administered to a patient in an amount in the range of about 100 μg–10,000 μg. These doses are based on the assumption that when interpulmonary delivery methodology is used the efficiency of the delivery is approximately 10% and adjustments in the amount released must be made in order to take into account the efficiency of the device. The differential between the amount of respiratory drug actually released from the device and the amount of respiratory drug actually delivered to the patient varies due to a number of factors. In general, the present device is approximately 20% efficient, however, the efficiency can be as low as 10% and as high as 50% meaning that as little as 10% of the released respiratory drug may actually reach the lungs of the patient and as much as 50% might be delivered. The efficiency of the delivery will vary somewhat from patient to patient and must be taken into account when programming the device for the release of respiratory drug. In general, a conventional metered dose inhaling device is about 10% efficient.

When administering respiratory drug using the inhalation device of the present invention, the entire dosing event can involve the administration of anywhere from 10 μl to 1,000 μl, but more preferably involves the administration of approximately 100 μl to 10,000 μl of formulation. The large variation in the amounts which might be delivered are due to the fact that different drugs have greatly different potencies and are present in formulations in different concentrations and may be delivered from devices which vary greatly in terms of the efficiency of drug delivered. The entire dosing event may involve several inhalations by the patient with each of the inhalations being provided with multiple bursts of respiratory drug from the device.

In addition to drug potency and delivery efficiency, respiratory drug sensitivity must be taken into consideration. The present invention makes it possible to vary dosing over time if asthma sensitivity changes and/or if user compliance and/or lung efficiency changes over time.

Based on the above, it will be understood that the dosing or amount of respiratory drug actually released from the device can be changed based on the most immediately prior monitoring event wherein the inspiratory flow of a patient's inhalation is measured.

Variations in doses are calculated by monitoring the effect of one or more lung function parameters in response to known amounts of respiratory drug released from the device. If the response in changing measured lung function parameters is greater than with previous readings, then the dosage is decreased or the minimum dosing interval is increased. If the response in changing measured lung function parameters is less than with previous readings, then the dosing amount is increased or the minimum dosing interval is decreased. The increases and decreases are gradual and are preferably based on averages (of 10 or more readings of lung function parameter after 10 or more dosing events) and not a single dosing event and monitoring event. The present invention can record dosing events and lung function parameters over time, calculate averages and deduce preferred changes in administration of respiratory drug.

One of the important features and advantages of the present invention is that the microprocessor can be programmed to take two different criteria into consideration with respect to dosing times. Specifically, the microprocessor can be programmed so as to include a minimum time interval between doses i.e. after a given delivery another dose cannot be delivered until a given period of time has passed. Secondly, the timing of the device can be programmed so that it is not possible to exceed the administration of a set maximum amount of drug within a given time. For example, the device could be programmed to prevent dispersing more than 200 mg of a particular respiratory drug within one hour. More importantly, the device can be programmed to take both criteria into consideration. Thus, the device can be programmed to include a minimum time interval between doses and a maximum amount of drug to be released within a given time period. For example, the microprocessor could be programmed to allow the release of a maximum of 200 mg of a given respiratory drug during an hour which could only be released in amounts of 25 mg with each release being separated by a minimum of five minutes.

The dosing program can be designed with some flexibility. For example, if the patient normally requires 250 μg per day of respiratory drug, the microprocessor of the inhalation device can be programmed to provide a warning after 250 μg have been administered within a given day and to continue the warning thereafter to alert the user of possible overdoses. By providing a warning and not a lock-out, the device would allow for the patient to administer additional respiratory drug, if needed, due to a decreased lung function and/or account for misdelivery of respiratory drug such as due to coughing or sneezing during an attempted delivery.

The ability to prevent overdosing is a characteristic of the device due to the ability of the device to monitor the amount of respiratory drug released and calculate the approximate amount of respiratory drug delivered to the patient based on monitoring a variety of lung function parameters. The ability of the present device to prevent overdosing is not merely a monitoring system which prevents further manual actuation of a button. As indicated above, the device used in connection with the present invention is not manually actuated, but is fired in response to an electrical signal received from a microprocessor (which received data from a monitoring device such as a device which monitors inspiratory flow) and allows the actuation of the device upon achieving an optimal point in a inspiratory cycle. When using the present invention, each release of the valve is a release which will administer drug to the patient in that the valve is released in response to patient inhalation. More specifically, the device does not allow for the release of respiratory drug merely by the manual actuation of a button to fire a burst of respiratory drug into the air or a container.

The microprocessor of applicant's invention will also include a timing device. The timing device can be electrically connected with visual display signals as well as audio alarm signals. Using the timing device, the microprocessor can be programmed so as to allow for a visual or audio signal to be sent when the patient would be normally expected to administer respiratory drug. In addition to indicating the time of administration (preferably by audio signal), the device can indicate the amount of respiratory drug which should be administered by providing a visual display. For example, the audio alarm could sound alerting the patient that respiratory drug should be administered. At the same time, the visual display could indicate "50 μg" as the amount of respiratory drug to be administered. At this point, a monitoring event could take place. After completion of the monitoring event, administration would proceed and the visual display would continually indicate the remaining amount of respiratory drug which should be administered. After the predetermined dose of 50 mg had been administered, the visual display would indicate that the dosing event had ended. If the patient did not complete the dosing event by administering the stated amount of respiratory drug, the patient would be reminded of such by the initiation of another audio signal, followed by a visual display instructing the patient to continue administration.

Additional information regarding dosing with respiratory drugs can be found within Harrison's—Principles of Internal Medicine (most recent edition) and the Drug Evaluation Manual, 1993 (AMA-Division of Drugs and Toxicology), both of which are published by McGraw Hill Book Company, New York, incorporated herein by reference to disclose conventional information regarding dosing respiratory drug.

Method of Administration

The method and device of the invention provides a number of features which make it possible to achieve the controlled and repeatable dosing procedure required for the treatment of respiratory diseases particularly when treated with drugs with a low therapeutic index. First, the membrane is permanently convex or is flexible and protrudes into fast moving air aiding the elimination of particle collisions. Second, the invention makes it possible to eliminate any carrier from the aerosolized particles and provide dry drug particles to a patient which particles can be manufactured to have a uniform size. By delivering particles of uniform size repeatability of dosing is enhanced regardless of the surrounding environment, e.g. different humidity conditions. Third, the device makes it possible to administer drug at the same point with respect to inspiratory flow rate and inspiratory volume at each drug delivery point thereby improving repeatability of dosing.

The method of the invention involves the release of a liquid, flowable drug from individual disposable containers which may be interconnected in a package. This is desirable in that the liquid, flowable drug is packaged under a sterile environment and therefore does not require and preferably does not include additional materials such as antifungal, bacteriostatics, and preservatives which would normally be required in a liquid formulation if the formulation was to be opened, exposed to air, closed and later used again. A new container and membrane are used for each release of drug. Thus, the membrane and container are disposable thereby preventing clogging of pores which takes place with reuse. The invention does not require the use of low boiling point propellants such as low boiling point fluorocarbons. The use of such low boiling point propellants in conventional metered dose inhaler devices is desirable because such propellants eliminate the need for preservatives, antifungal and bacteriostatic compounds. However, there are potential environmental risks to using low boiling point fluorocarbons. Accordingly, the present invention provides potential environmental benefits and would be particularly useful if government regulations prevented further use of devices which dispensed low boiling point fluorocarbons.

In addition to environmental advantages, the present invention offers advantages due to the relatively slow speed at which the aerosol dispersion is delivered to the patient. A conventional metered dose inhaler device discharges the aerosol outward at a relatively high rate of speed which causes a large amount of the aerosol particles to make contact with the inside of the patient's mouth and the back of the patient's throat. This decreases the amount of drug actually administered to the patient's lungs as compared with the present system, wherein the aerosol is delivered at a relatively slow rate of speed and can be inhaled slowly by the patient.

The method preferably uses a drug delivery device which is not directly actuated by the patient in the sense that no button is pushed nor valve released by the patient applying physical pressure. On the contrary, the device of the invention provides that the actuation mechanism which causes drug to be forced from a container is fired automatically upon receipt of a signal from a microprocessor programmed to send a signal based upon data received from a monitoring device such as an airflow rate monitoring device. A patient using the device withdraws air from a mouthpiece and the inspiratory rate, and calculated inspiratory volume of the patient is measured simultaneously one or more times in a monitoring event which determines an optimal point in an inhalation cycle for the release of a dose of any desired drug. Inspiratory flow is preferably measured and recorded in one or more monitoring events for a given patient in order to develop an inspiratory flow profile for the patient. Recorded information is preferably analyzed by the microprocessor in order to deduce a preferred point within the patient's inspiratory cycle for the release of drug with the preferred point being calculated based on the most likely point to result in a reproducible delivery event.

A flow rate monitoring device continually sends information to the microprocessor, and when the microprocessor determines that the optimal point in the respiratory cycle is reached, the microprocessor actuates a component which fires a mechanical means (and activates the vibration device) which causes drug to be forced out of the container and aerosolized. Accordingly, drug is repeatedly delivered at a pre-programmed place in the inspiratory flow profile of the particular patient which is selected specifically to maximize reproducibility of drug delivery and peripheral deposition of the drug. It is pointed out that the device of the present invention can be used to, and actually does, improve the efficiency of drug delivery. However, this is not the most important feature. A more important feature is the reproducibility of the release of a tightly controlled amount of drug (with a narrow range of particle size) repeatedly at the same particular point in the respiratory cycle so as to assure the delivery of a controlled and repeatable amount of drug to the lungs of each individual patient, i.e. intrapulmonary drug delivery with tightly controlled dosing. The heating component(s) and/or the desiccator to remove water vapors aid in providing repeatability in dosing in that the particles reaching the patient will have the same size regardless of the surrounding humidity. By keeping the particle size the same at each dosing event the particles deposit at the same general area of the lung at each event. These features improve repeatability along with automatic control of the drug release mechanism, combined with frequent monitoring events in order to calculate the optimal flow rate and time for the release of respiratory drug. Further, the particles will have uniform size in that all carrier is removed regardless of the humidity of the surrounding environment. Because the drug release mechanism is fired automatically and not manually, it can be predictably and repeatedly fired at that same point in the inspiratory cycle. Because dosing events are preferably preceded by monitoring events, the point in the inspiratory cycle of the release can be readjusted based on the particular condition of the patient. For example, patients suffering from asthma have a certain degree of pulmonary insufficiency which may well change with the administration of drug. These changes will be taken into account in the monitoring event by the microprocessor which will readjust the point of release of the respiratory drug in a manner calculated to provide for the administration of an amount of respiratory drug to the patient presently needed by the patient at each dosing event.

When administering drug using the inhalation device of the present invention, the entire dosing event can involve the administration of anywhere from 10 $\mu$l to 1,000 ml of drug formulation, but more preferably involves the administration of approximately 50 $\mu$l to 10,000 $\mu$l of drug formulation. Very small amounts of drug (e.g., nanogram amounts) may be dissolved or dispersed within a pharmaceutically acceptable, liquid, excipient material to provide a liquid, flowable formulation which can be readily aerosolized. The container will include the formulation having drug therein in an amount of about 10 ng to 300 $\mu$g, more preferably about 50 $\mu$g. The large variation in the amounts which might be delivered are due to different drug potencies and different delivery efficiencies for different devices, formulations and patients. The entire dosing event may involve several inhalations by the patient with each of the inhalations being provided with drug from the device. For example, the device can be programmed so as to release the contents of a single container or to move from one container to the next on a package of interconnected containers. Delivering smaller amounts from several containers can have advantages. Since only small amounts are delivered from each container and with each inhalation, even a complete failure to deliver drug with a given inhalation is not of great significance and will not seriously disturb the reproducibility of the dosing event. Further, since relatively small amounts are delivered with each inhalation, the patient can safely administer a few additional micrograms of drug (or milligrams for some drugs) without fear of overdosing.

In addition to drug potency and delivery efficiency, drug sensitivity must be taken into consideration. The present invention makes it possible to vary dosing over time if sensitivity changes and/or if user compliance and/or lung efficiency changes over time.

Based on the above, it will be understood that the dosing or amount of drug (and in particular respiratory drug) actually released from the device can be changed based on the most immediately prior monitoring event wherein the inspiratory flow of a patient's inhalation is measured.

Variations in doses are calculated by monitoring the effect of one or more lung function parameters in response to known amounts of respiratory drug released from each container and delivered to the patient. If the response in changing measured lung function parameters is greater than with previous readings, then the dosage (number of containers released) is decreased or the minimum dosing interval is increased. If the response in changing measured lung function parameters is less than with previous readings, then the dosing amount is increased or the minimum dosing interval is decreased. The increases and decreases are gradual and are preferably based on averages (of 10 or more readings of lung function parameter after 10 or more dosing events) and not a single dosing event and monitoring event. The preferred drug delivery device of the present invention can record dosing events and lung function parameters over time, calculate averages and deduce preferred changes in administration of respiratory drug.

One of the important features and advantages of the present invention is that the microprocessor can be programmed to take a number of different criteria into consideration with respect to dosing times. For example, the microprocessor can be programmed so as to include a minimum time interval between doses i.e. after a given delivery another dose cannot be delivered until a given period of time has passed. Secondly, the timing of the device can be programmed so that it is not possible to exceed the administration of a set maximum amount of drug within a given time. For example, the device could be programmed to prevent dispersing more than 200 μg (or two 100 μg containers) of a particular drug within one hour. More importantly, the device can be programmed to take both criteria into consideration. Thus, the device can be programmed to include a minimum time interval between doses and a maximum amount of drug to be released within a given time period. For example, the microprocessor could be programmed to allow the release of a maximum of 200 μg of a given drug during an hour which could only be released in amounts of 25 μg with each release being separated by a minimum of five minutes.

The dosing program can be designed with some flexibility. For example, if the patient normally requires 250 μg per day of respiratory drug, the microprocessor of the inhalation device can be programmed to provide a warning after 250 μg have been administered within a given day and to continue the warning thereafter to alert the user of possible overdoses. By providing a warning and not a lock-out, the device allows for the patient to administer additional respiratory drug, if needed, due to a decreased lung function and/or account for misdelivery of respiratory drug such as due to coughing or sneezing during an attempted delivery.

The ability to prevent overdosing is a characteristic of the device due to the ability of the device to monitor the amount of respiratory drug released and calculate the approximate amount of respiratory drug delivered to the patient based on monitoring a variety of lung function parameters. The ability of the present device to prevent overdosing is not merely a monitoring system which prevents further manual actuation of a button. As indicated above, the device used in connection with the present invention is not manually actuated, but is fired in response to an electrical signal received from a microprocessor (which received data from a monitoring device such as a device which monitors inspiratory flow) and allows the actuation of the device upon achieving an optimal point in a inspiratory cycle. When using the present invention, each actuation of the device will administer drug to the patient in that the device is fired in response to patient inhalation. More specifically, the preferred embodiment of the device does not allow for the release of respiratory drug merely by the manual actuation of a button to fire a burst of respiratory drug into the air or a container.

A variety of different embodiments of the dispersion device of the invention are contemplated. In accordance with one embodiment it is necessary to carry out manual cocking of the device. This means that energy is stored such as by retracting a spring so that, for example, a piston can be positioned below the drug containing container. In a similar manner a piston connected to a spring can be withdrawn so that when it is released it will force air through the air dispersion vents. Automatic cocking of forced storing systems for both the drug formulation and the air flow may be separate or in one unit. Further, one may be manual whereas the other may be done automatically. In accordance with one embodiment the device is cocked manually but fired automatically and electronically based on monitoring the patients inspiratory flow. The formulation may be physically moved through the porous membrane in a variety of different ways. Formulation may be forced through the membrane by a piston or, without applying force to the formulation, the membrane being vibrated at frequencies sufficient to create an aerosol.

The microprocessor 26 of the present invention preferably includes a timing device. The timing device can be electrically connected with visual display signals as well as audio alarm signals. Using the timing device, the microprocessor can be programmed so as to allow for a visual or audio signal to be sent when the patient would be normally expected to administer respiratory drug. In addition to indicating the time of administration (preferably by audio signal), the device can indicate the amount of respiratory drug which should be administered by providing a visual display. For example, the audio alarm could sound alerting the patient that respiratory drug should be administered. At the same time, the visual display could indicate "one dosage unit" as the amount of drug (number of containers) to be administered. At this point, a monitoring event could take place. After completion of the monitoring event, administration would proceed and the visual display would continually indicate the remaining amount of respiratory drug which should be administered. After the predetermined dose (indicated number of containers) had been administered, the visual display would indicate that the dosing event had ended. If the patient did not complete the dosing event by administering the stated amount of drug, the patient would be reminded of such by the initiation of another audio signal, followed by a visual display instructing the patient to continue administration.

Additional information regarding dosing with drugs can be found within Harrison's—Principles of Internal Medicine (most recent edition) and the Drug Evaluation Manual, 1993 (AMA-Division of Drugs and Toxicology), both of which are published by McGraw Hill Book Company, New York, incorporated herein by reference to disclose conventional information regarding dosing of drugs and in particular respiratory drugs as well as other useful drugs and formulations.

Supplemental Treatment Methodology

The present invention can be used to deliver many types of drugs. Specifically, the disposable containers, packages, and drug delivery devices can be used to deliver drugs which have a systemic effect (e.g. narcotics, proteins such as insulin and antibiotics) as well as drugs which have a local effect primarily on the lungs (e.g. bronchodilators DNAse or steroids). Because the present invention allows drug delivery directly to the lungs there are certain advantages with respect to using the invention for the delivery of drugs to treat respiratory diseases. For this reason, much of the operation of the invention is described in connection with the delivery of respiratory drugs. However, the invention is not limited to respiratory drugs and the examples described herein would apply with respect to the delivery of drugs having a systemic effect. This is true also with respect to the supplemental treatment methodology described below even though this methodology is described with specific reference to respiratory diseases being treated with respiratory drugs.

Patients suffering from a given disease such as a respiratory disease may be treated solely with respiratory drug as indicated above, i.e. by intrapulmonary delivery. However, it is possible to treat such patients with a combination of intrapulmonary delivery and other means of administration such as oral administration. The oral drug is preferably given in amount so as to maintain a baseline level of drug within the circulatory system which is sufficient to maintain body functions such as lung function at an acceptable level. However, this baseline level of drug to blood ratio (or serum blood level) must be raised in order to improve the body function such as lung function during periods of stress such as respiratory difficulty such as an asthma attack and such can be accomplished by the intrapulmonary administration of a drug such as a respiratory drug using the present invention.

Based on the above, it will be understood by those skilled in the art that a plurality of different treatments and means of administration can be used to treat a single patient. For example, a patient can be simultaneously treated with respiratory drug by transdermal administration, respiratory drug via intrapulmonary administration in accordance with the present invention, and drugs which are orally administered.

The device 40 schematically shown within FIG. 4 can be specifically operated as follows. A container 1 is loaded into the device 6. The device is then armed meaning that the piston such as the spring-loaded piston 24 is cocked. If applicable another piston (not shown) used to compress the liquid formulation in a dual container system is cocked. Further, a container 1 of the package is moved into position and any cover is stripped off of the porous membrane 3. Thereafter, the patient withdraws air from the mouthpiece 30 and the patient's inhalation profile is developed using the microprocessor 26. After the inhalation profile is determined, the microprocessor calculates a point within the inhalation profile at which the drug should be released in order to maximize repeatability of the dosing, e.g. by plotting a curve of breath velocity versus time and determining the point on the curve most likely to provide repeatability of dosing. However, in order to carry out methodology in accordance with the present invention it is not necessary to plot any curve of breath velocity versus time. The device can be set so that the dose will be repeatedly released at approximately the same point with respect to inspiratory flow rate and inspiratory volume. If the device repeatedly fires at the same inspiratory flow rate and inspiratory volume each time the patient will receive substantially the same dose. Both criteria must be measured and used for firing to obtain repeatability.

Further details with respect to obtaining improved repeatability of dosing in addition to improved delivery efficiency are disclosed within related application entitled: "Intrapulmonary Drug Delivery Within Therapeutically Relevant Inspiratory Flow/Volume Values" filed on Jul. 11, 1994, U.S. Ser. No. 08/273,375 which application is incorporated herein by reference. The microprocessor of the present invention can be programmed to release drug based on all or any of the following parameters.

(1) Delivery should be at an inspiratory flow rate inside a range of about 0.10 to about 2.0 liters per second (efficiency can be obtained by delivering at a flow rate in a range of 0.2 to about 1.8 liters per second and more preferably 0.15 to 1.7 liters per second). Repeatability of the delivery is obtained by releasing at substantially the same inspiratory flow rate at each drug release.

(2) Delivery should be at a point within a patient's inspiratory volume of about 0.15 to about 2.0 liters (further efficiency of delivery can be obtained by delivering within a range of 0.15 to 0.8 liters and more preferably 0.15 to about 0.4 liters). Repeatability of delivery is obtained by delivering at the same inspiratory volume at each release of drug.

(3) Delivery is improved by providing a system which creates particles for systemic delivery wherein the particles are in the range of about 0.5 to about 12.0 microns, preferably 0.5 to 6 microns and more preferably 0.5 to about 3 microns. The size is somewhat larger for pulmonary delivery i.e., delivery to the lung surface for treatment so that the particles should in the range of 0.5 to 12 microns, preferably 2.0 to 7 microns and more preferably 2.0 to 5.0 microns.

(4) It is desirable to have obtained a concentration of the drug in the carrier in the range of from about 0.01 to about 12.5% preferably 0.1 to 10%. By maintaining the concentration of drug to carrier in this range it is possible to create particles which are somewhat larger than would be desirable for delivery but to reduce those particles in size by evaporation of carrier.

(5) Air drawn into the flow path of the aerosolized particles is heated by adding energy to each 10 $\mu$l of formulation in an amount of about 20 Joules to 100 Joules, more preferably 20 Joules to 50 Joules. The heated air aids in reducing the effect of humidity and evaporates carrier away from the particles thereby providing smaller particles for inhalation.

(6) Air is added to the aerosolized formulation by the patient drawing air into the aerosolized mist in an amount of about 100 milliliters to 2 liters per 10 microliters of aerosol formulation.

(7) Vibration may be created on the porous membrane in an amount 575 to 32,000, preferably 1,000 to 17,000 and more preferably 2,000 to 4,000 kilohertz.

(8) The pore size of the membrane is regulated within a range of 0.25 to about 6.0 microns, preferably 0.5 to 3 microns and more preferably 1 to 2 microns. This size refers to the diameter of the pore through which the formulation exits the membrane. The diameter of the opening into which the formulation flows may be 2 to 20 times that size in diameter thereby providing a conical configuration.

(9) The viscosity of the formulation affects the amount of pressure which needs to be applied to force the formulation through the pores and should be within the range of 25% to 1,000% the viscosity of water.

(10) The extrusion pressure is regulated within a range of 50 to 600 psi more preferably 100 to 500 psi. Lower pressures may be obtained by using the conical configuration for the pore size.

(11) The microprocessor should also be provided information regarding the ambient temperature and atmospheric pressure. The temperature is preferably close to room temperature i.e., within a range of 15° C. to 30° C. An atmospheric pressure is generally 1 atmosphere or slightly lower at higher altitudes, e.g., about 75% of 1 atmosphere.

(12) To provide for consistency in dosing the ratio of the carrier to drug should be maintained constant and more highly soluble drugs are more desirable. However, it is possible to use drugs that are insoluble by creating suspensions or by using solubility enhancers.

(13) A desiccator is preferably used to remove water vapor from air drawn into the flow path by the patient.

(14) The pores are preferably placed in the porous membrane in an elongated oval or elongated rectangular configuration. By configuring the pores in this manner and drawing air perpendicularly over the narrower dimension of the configuration it is possible to reduce the amount of collisions between particles and thereby avoid particles collision resulting in accumulation.

(15) The thickness of the membrane is preferably regulated in the range of 5 to 200 microns or more preferably 10 to 50 microns. Thinner membranes are useful in that less pressure is required to force formulation through the membrane. The membrane has a tensile strength of 5,000 to 20,000, preferably 8,000 to 16,000 and more preferably 14,000 to 16,000 psi.

(16) The membrane is configured so as to have a convex configuration which protrudes into faster moving air created by the patient's inhalation or is designed to be flexible so that it will assume a convex configuration when formulation is forced through the membrane.

(17) After the microprocessor is provided information with respect to above parameters or measurements a drug release point is chosen and the microprocessor will continually return to substantially the same firing point at each drug delivery so as to obtain repeatability of dosing.

After drug has been delivered it is possible to discontinue any readings with respect to flow and/or volume. However, it is preferable to continue readings with respect to both criteria after drug has been released. By continuing the readings the adequacy of this patient's particular drug delivery maneuver can be determined. All of the events are recorded by the microprocessor. The recorded information can be provided to the caregiver for analysis. For example, the caregiver can determine if the patient correctly carried out the inhalation maneuver in order to correctly delivery drug and can determine if the patient's inhalation profile is effected by the drug (e.g. with respiratory drugs) in order to determine the effectiveness of the drug in treating the patient's particular condition. If necessary, various adjustments can be made such as in the type of drug or the particle size to obtain a particular desired result.

The instant invention is shown and described herein in which is considered to be the most practical and preferred embodiments. It is recognized, however, that the departures may be made therefrom which are within the scope of the invention and that obvious modifications will occur to one skilled in the art upon reading this disclosure.

What is claimed is:

1. A disposable container for use in creating an aerosolized burst of respiratory drug formulation, comprising:

a wall which is collapsible upon the application of force;

an opening in the container, which opening is covered at least in part by a porous membrane having pores with a diameter in the range of about 0.25 to about 6.0 microns, the membrane being sufficiently flexible such that it will protrude outward in a convex configuration upon the application of force; and a respiratory drug formulation comprised of a pharmaceutically active respiratory drug and a carrier which formulation is characterized by its ability to form an aerosol of particles which can be inhaled into a patient's lungs when the formulation is moved through the pores of the membrane.

2. The container of claim 1, wherein the opening forms an open channel leading from the opening to a breakable seal beyond which is an area covered by the porous membrane and further wherein the pores have a cross-sectional configuration with a small end opening of 0.25 to 6.0 microns in diameter and a large end opening of 2 to 20 times the diameter of the small end.

3. The container of claim 1, wherein the porous membrane is flexible and protrudes outward in a convex configuration when the formulation is moved through the membrane.

4. The container of claim 1, wherein the porous membrane has a convex configuration.

5. A disposable package comprising a plurality of interconnected disposable containers as claimed in claim 1 wherein each container has therein a respiratory drug selected from the group consisting of isoproterenol, cromolyn, albuterol, metaproterenol, terbutaline, pirbuterol, salmeterol xinotoate, formotorol, beclomethasone dipropionate, triamcinolone acetonide, flunisolide, fluticasone, budesonide, ipratropium bromide, and free acids, bases, salts and hydrates thereof, and peptide non-adrenergic non-cholinergic neurotransmitters, anticholinergics, leukotriene inhibitors, vasoactive intestinal peptide, tachykinin antagonists, bradykinin antagonists, endothelin antagonists, heparin furosemide, anti-adhesion molecules, cytokine modulators, biologically active endonucleases, recombinant human (rh) DNase compounds, α antitrypsin, and disodium cromoglycate.

6. A method for creating an aerosol, comprising:

drawing air through a channel and over a surface of a flexible, disposable, porous membrane having pores with a diameter in the range of about 0.25 to about 6.0 microns;

forcing a formulation comprised of a pharmaceutically active respiratory drug and a carrier through the pores of the membrane with sufficient force as to protrude the membrane outward in a convex configuration away from the formulation and toward the air drawn through the channel;

wherein the flexible membrane protrudes outward beyond a boundary layer of air flow created in the channel and the air is drawn over the protruded membrane to a channel end, via a substantially linear flow path.

7. The method of claim 6, further comprising:

measuring airflow through the channel and determining inspiratory flow rate and inspiratory volume; and determining a beginning point to force formulation through the pores of the membrane based on real time values of inspiratory flow rate and inspiratory volume.

8. The method of claim 7, further comprising:

repeating the drawing, measuring, determining and forcing steps in a manner such that the forcing repeatedly begins at substantially the same inspiratory flow rate and inspiratory volume wherein the forcing occurs at an inspiratory flow rate in the range of about 0.10 to about 2.0 liters/second and an inspiratory volume in the range of about 0.15 to about 1.5 liters;

adding energy to the aerosolized particles by actively heating air brought into contact with the particles; and inhaling the particles into the lungs of a patient;

wherein energy is added in an amount such that 50% or more of the carrier in the particles when formed is evaporated prior to the particles reaching the patient and wherein the energy is added by actively heating air by moving air through a heated material which material is heated prior to the patient's inhalation.

* * * * *